(12) United States Patent
Meskens et al.

(10) Patent No.: US 9,020,601 B2
(45) Date of Patent: Apr. 28, 2015

(54) HEARING PROSTHESIS WITH A STANDARD WIRE INTERFACE

(75) Inventors: Werner Meskens, Opwijk (BE); Erika Van Baelen, Leuven (BE); Koen Van den Heuvel, Hove (BE); Peter Van Gerwen, Keerbergen (BE)

(73) Assignee: Cochlear Limited, Macquarie University, NSW (AU)

( * ) Notice: Subject to any disclaimer, the term of this patent is extended or adjusted under 35 U.S.C. 154(b) by 86 days.

(21) Appl. No.: 13/555,358

(22) Filed: Jul. 23, 2012

(65) Prior Publication Data

US 2014/0025138 A1    Jan. 23, 2014

(51) Int. Cl.
*A61N 1/05* (2006.01)
*A61N 1/36* (2006.01)
*A61N 1/372* (2006.01)

(52) U.S. Cl.
CPC ......... *A61N 1/36032* (2013.01); *A61N 1/37247* (2013.01)

(58) Field of Classification Search
USPC .......................................................... 607/57
See application file for complete search history.

(56) References Cited

U.S. PATENT DOCUMENTS

| 5,824,022 | A | 10/1998 | Zilberman |
| 6,560,488 | B1 | 5/2003 | Crawford |
| 2005/0010267 | A1* | 1/2005 | Ibrahim ........................ 607/57 |
| 2006/0153395 | A1 | 7/2006 | Van den Heuvel et al. |
| 2007/0282392 | A1 | 12/2007 | Callias et al. |
| 2009/0215502 | A1 | 8/2009 | Griffin, Jr. |
| 2009/0245566 | A1 | 10/2009 | Jheng |
| 2010/0046778 | A1 | 2/2010 | Crawford et al. |
| 2010/0046779 | A1 | 2/2010 | Crawford et al. |
| 2012/0041515 | A1 | 2/2012 | Meskens |
| 2012/0095528 | A1 | 4/2012 | Miller et al. |
| 2012/0197065 | A1* | 8/2012 | Botros et al. ..................... 600/25 |

FOREIGN PATENT DOCUMENTS

JP    2001-511409 A    8/2001

OTHER PUBLICATIONS

International Search Report and Written Opinion for PCT/IB2013/056005 dated Mar. 20, 2014.

* cited by examiner

*Primary Examiner* — Carl H Layno
*Assistant Examiner* — Jon Eric C Morales
(74) *Attorney, Agent, or Firm* — McDonnell Boehnen Hulbert & Berghoff LLP

(57) ABSTRACT

Methods, systems, and devices for receiving a data signal and a power signal by a hearing prosthesis are disclosed. An input signal is received at a first unit of a hearing prosthesis. The first unit receives the input signal at a wired interface module that conforms to a standardized interface. The first unit identifies a data signal and a power signal included in the input signal. The first unit transfers at least a portion of the power signal to a second unit of the hearing prosthesis. The second unit is implanted in a body and is configured to stimulate an auditory organ, allowing a user to perceive at least a portion of a sound.

16 Claims, 11 Drawing Sheets

HEARING PROSTHESIS WITH A STANDARD WIRE INTERFACE

BACKGROUND

Individuals who suffer from certain types of hearing loss may benefit from the use of a hearing prosthesis. Depending on the type and the severity of the medical condition, an individual can employ a hearing prosthesis to assist the user in perceiving at least a portion of a sound. A partially implantable hearing prosthesis typically includes an external component that performs at least some processing functions and an implanted component that at least delivers a stimulus to an auditory organ, such as a cochlea, an auditory nerve, a brain, or any other organ that contributes to the perception of sound. In the case of a totally implantable hearing prosthesis, the entire device is implanted in the body of the user.

For a partially implantable hearing prosthesis, the external component receives a sound and generates a stimulation signal based on the sound. The stimulation signal includes information indicative of the stimulus to be applied to the auditory organ. The external component sends the stimulation signal to the implanted component. The external component also sends a power signal to the implanted component. The power signal provides power to one or more subcomponents of the implanted component. The implanted component receives the stimulation signal and the power signal, and generates the stimulus based on the stimulation signal. Applying the stimulus to the auditory organ allows a user of the partially implantable hearing prosthesis to perceive at least a portion of the sound.

SUMMARY

A method for receiving a power signal and a data signal at a wired interface module that conforms to a standardized interface is disclosed. The method includes receiving, at a first unit of a hearing prosthesis, an input signal. The first unit receives the input signal at a wired interface module that conforms to a standardized interface. The method also includes identifying a power signal included in the input signal and identifying a data signal included in the input signal. The method additionally includes transferring at least a portion of the power signal from the first unit to a second unit of the hearing prosthesis. The second unit is implanted in a body and is configured to stimulate an auditory organ.

A first system is disclosed. The first system includes an implanted unit configured to deliver a stimulus to an auditory organ. The first system also includes a headpiece unit. The headpiece unit includes a first wired interface module having a first receptacle. The headpiece unit is configured to transmit a stimulation signal that includes information indicative of the stimulus to the implanted unit. The headpiece unit is also configured to transfer at least a portion of a power signal to the implanted unit. Additionally, the first system includes a processing unit. The processing unit includes a second wired interface module having a second receptacle. The processing unit is configured to generate the stimulation signal based on a sound. The processing unit is also configured to transfer the stimulation signal and the power signal to the headpiece unit via a cable. The cable includes a first plug that is inserted into the first receptacle and a second plug that is inserted into the second receptacle. At least one of the first wired interface module and the second wired interface module conforms to a standardized interface.

A second system is also disclosed. The second system includes an implanted unit configured to deliver a stimulus to an auditory organ. The second system also includes a processing unit. The processing unit is configured to receive, at a wired interface module that conforms to at least one standardized interface, an input signal from a remote device. The input signal includes a data component and a power component. The processing unit is also configured to separate the input signal into the data component and the power component. The processing unit is further configured to transfer at least a portion of the power component to the implanted unit.

A first device is disclosed. The first device includes a transceiver configured to transmit a stimulation signal to an implanted unit of a hearing prosthesis. The stimulation signal includes information indicative of a stimulus to be delivered to an auditory organ. The first device also includes an induction coil configured to transfer at least a portion of a power signal to the implanted component. The first device additionally includes a wired interface module. The wired interface module is configured to receive an input signal that includes the stimulation signal and the power signal. The wired interface module conforms to at least one standardized interface. The first device further includes an interface processor. The interface processor is configured to receive the input signal from the wired interface module. The interface processor is also configured to separate the input signal into the stimulation signal and the power signal. The interface processor is further configured to route the stimulation signal to the transceiver and to route at least a portion of the power signal to the induction coil.

A second device is also disclosed. The second device includes a wired interface module that conforms to a standardized interface. The second device also includes a power supply. The second device additionally includes one or more processors. The one or more processors are configured to receive a data signal from a remote device via the wired interface module. The one or more processors are also configured to receive a power signal from the remote device via the wired interface module. The one or more processors are additionally configured to process the data signal. The one or more processors are further configured to transfer at least a portion of the power signal to the power supply.

These as well as other aspects and advantages will become apparent to those of ordinary skill in the art by reading the following detailed description, with reference where appropriate to the accompanying drawings. Further, it is understood that this summary is merely an example and is not intended to limit the scope of the invention as claimed.

BRIEF DESCRIPTION OF THE FIGURES

Presently preferred embodiments are described below in conjunction with the appended drawing figures, wherein like reference numerals refer to like elements in the various figures, and wherein.

DETAILED DESCRIPTION

The following detailed description describes various features, functions, and attributes of the disclosed systems, methods, and devices with reference to the accompanying figures. In the figures, similar symbols typically identify similar components, unless context dictates otherwise. The illustrative embodiments described herein are not meant to be limiting. Certain aspects of the disclosed systems, methods, and devices can be arranged and combined in a wide variety of different configurations, all of which are contemplated herein.

1. Example Hearing Prostheses

Figure 1A:
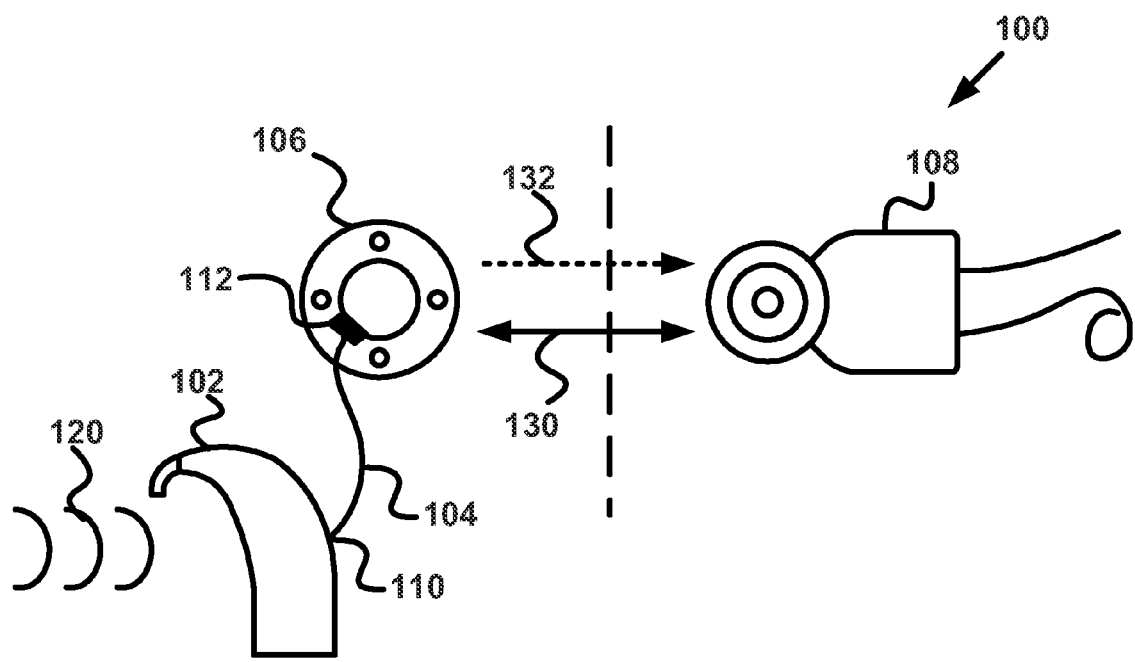
FIG. 1A illustrates components of a first hearing prosthesis, according to an example.

FIG. 1A illustrates a first hearing prosthesis 100. The hearing prosthesis 100 includes a processing unit 102, a cable 104, a headpiece unit 106, and an implanted unit 108. A user utilizes the hearing prosthesis 100 to assist the user in perceiving a sound. In FIG. 1A, the hearing prosthesis 100 is a partially implantable cochlear implant. The processing unit 102, the cable 104, and the headpiece unit 106 are external to the user's body. The implanted unit 108 is implanted in the user's body. In another example, the hearing prosthesis 100 is a bone conduction device, direct acoustic stimulation device, an auditory brain stem implant, a middle ear implant, or any other hearing prosthesis or combination of hearing prostheses now known or later developed.

The processing unit 102 receives a sound 120. In one example, the sound 120 originates from a source in an environment. The processing unit 102 includes a component capable of receiving the sound 120, such as an audio transducer. In another example, the sound 120 originates from an external device configured to send the sound signal to the processing unit 102, such as an audio streaming device. In this example, the processing unit 102 includes a component configured to receive the sound 120 from the external device, such as a wired or wireless interface component.

The processing unit 102 processes the sound 120 and generates a stimulation signal based on the sound. The processing unit 102 also provides power to both the implanted unit 106 and the implanted unit 108. The processing unit 102 sends an input signal to the headpiece unit 106 via the cable 104 that includes the stimulation signal and a primary power signal. In one example, the processing unit 102 sends the input signal to the headpiece unit 104 using a standardized data protocol. The standardized data protocol represents a protocol established by an industry-recognized governing body for simultaneously transferring data or transferring data and power. The standardized data protocol is a Universal Serial Bus ("USB") data protocol, a Universal Asynchronous Receiver/Transmitter ("UART") protocol, a Universal Synchronous/Asynchronous Receiver/Transmitter ("USART") protocol, or any other standardized data protocol now known or later developed that is suitable for simultaneously transmitting data and power.

In the example depicted in FIG. 1A, a first end 110 of the cable 104 is permanently connected to the processing unit 102. A second end of cable 104 includes a first plug 112. The first plug 112 is inserted into a first receptacle located on the headpiece unit 106 to connect the processing unit 102 to the headpiece component 106.

In one example, the first plug 112 and the first receptacle conform to a standardized physical interface. As used throughout this description, the standardized physical interface is a physical shape for a serial interface established by an industry-recognized governing body. The standardized physical interface is a Universal Serial Bus (USB) serial interface, an RS-232 serial interface (which, as used throughout this description, includes a level-converted transistor-transistor logic interface or a level-converted complimentary metal-oxide-semiconductor logic interface) or any other standardized physical interface suitable transferring data and power. In one example, the first plug 112 is a USB Micro-A plug, and the first receptacle is a USB Micro-A receptacle. In another example, the first plug 112 is a USB Micro-B plug, and the first receptacle is a USB Micro-B receptacle. In yet another example, the first plug 112 and the first receptacle are any plug and associated receptacle now know or later developed that conform to a USB interface.

In another example, the first plug 112 and the first receptacle conform to a standardized electrical interface. As used throughout this description, the standardized electrical interface represents a standardized serial interface that conforms to one or more electrical specifications for as defined by an industry-recognized governing body. For instance, the standardized electrical interface is a USB electrical interface, RS-232 interface, or any other standardized electrical interface suitable for simultaneously transferring data and power.

In another example, the first end 110 of the cable 104 is not permanently connected to the processing unit 102. In this example, the first end 110 includes a second plug that connects to a second receptacle located on the processing unit 102. In one example, the second plug and the second receptacle conform to a standardized physical interface associated with the first plug and first receptacle. For example, if the first plug 112 and the first receptacle are a USB Micro-A plug and a USB Micro-A receptacle, respectively, the second plug and the second receptacle are a USB Micro-B plug and a USB Micro-B receptacle. Alternatively, the second plug and the second receptacle conform to a standardized physical interface that is not associated with the standardized physical interface of the first plug and the first receptacle. In yet another example, at least one set of plugs and receptacles (e.g., first plug-first receptacle, second plug-second receptacle) conform to a proprietary physical interface.

The cable 104 includes wiring suitable for transferring the transmission signal from the processing unit 102 to the headpiece unit 106. The cable includes at least one wire suitable for transferring a data signal and at least one wire suitable for transferring a power signal. In one example, the wiring of the cable 104 conforms to a standardized electrical interface, such as a USB serial interface, an RS-232 electrical serial interface, or any other standardized electrical interface suitable for simultaneously transferring data and power. For example, if the cable 104 conforms to a USB electrical interface specification, the cable 104 includes at least a pair of wires for sending and receiving data between the processing unit 102 to the headpiece unit 106, a third wire for transferring a five volt power signal from the processing unit 102 to the headpiece unit 106, and a fourth wire that is grounded.

The headpiece unit 106 receives the input signal from the processing unit 102 via the cable 104. The headpiece unit 106 separates the components of the input signal into the stimulation signal and the primary power signal. The headpiece unit 106 uses a portion of the primary power signal to power one or more components of the headpiece unit 106.

The headpiece unit 106 transfers a second portion of the primary power signal, which is illustrated as a secondary power signal 132 and may constitute the remainder of the primary power signal, to the implanted unit 108 via an inductive coil. The headpiece unit 106 also transmits the stimulation signal to the implanted unit 108 via a transcutaneous link 130. In one example, the headpiece unit 106 transmits the stimulation signal using the inductive coil. That is, the headpiece unit 106 modulates the power signal based on the stimulation signal such that power signal contains the stimulation signal. In another example, the headpiece unit 106 transmits the stimulation signal at a frequency in the radio frequency ("RF") range, such as a frequency of about 2.4 GHz. In yet another example, the headpiece unit 106 transmits the stimulation signal in any medium suitable for communications via the transcutaneous link 130.

The implanted unit 108 receives the stimulation signal and the secondary power signal 132 from the headpiece unit 106. The implanted unit 108 creates a stimulus based on the stimulation signal. The implanted unit 108 delivers the stimulus to an auditory organ, such as a cochlea, an auditory nerve, a brain, or any other organ or body part capable of being stimulated to assist the user in perceiving at least a portion of a sound.

Delivering the stimulus to the auditory organ stimulates the auditory organ allows the user to perceive at least a portion of the sound 120. In one example, the stimulus is an electrical stimulus. In another example, the stimulus is a mechanical stimulus. In yet another example, the stimulus is any stimulus capable of stimulating an auditory organ so as to allow the user to perceive at least a portion of the sound.

In FIG. 1A, the hearing prosthesis 100 is a partially implantable cochlear implant. The implanted unit 108 includes an electrode array that is inserted into a portion of the user's cochlea. Upon receiving the stimulation signal, the implanted unit 108 generates an electrical signal based on the stimulation signal. The implanted unit 108 sends the electrical signal to the electrode array. The electrical signal causes one or more electrodes of the electrode array to electrically stimulate the cochlea. The stimulus to the cochlea causes the cochlea to stimulate an auditory nerve, thereby allowing the user to perceive the sound 120. In another example, the hearing prosthesis 100 is part of a different hearing prosthesis. In this example, the implanted unit 108 delivers the stimulus 140 to a different body part, such as an auditory nerve or a portion of the user's brain that processes auditory impulses. Delivery of the stimulus 140 to the different body part allows the user's to perceive at least a portion of the sound 120.

The implanted unit 108 is also configured to monitor a plurality of parameters associated with generating and delivering the stimulus. The plurality of parameters may include an output voltage, an output current, a line impedance, or any other parameter associated with generating and delivering the stimulus. The implanted unit 108 generates a telemetry signal that includes information indicative of one or more parameters of the plurality of parameters. The implanted unit transmits the telemetry signal to the headpiece unit 106 via the first transcutaneous link 130.

The headpiece unit 106 receives the telemetry signal and transfers the telemetry signal to the processing unit 102 via the cable 104. In one example, the processing unit 102 utilizes the telemetry signal to verify proper operation of the implanted unit 108. In another example, the telemetry signal is used for fitting or calibrating the hearing prosthesis 100. The processing unit 102 transfers the telemetry signal to an external device that is also connected to the processing unit 102. In yet another example, the processing unit 102 stores the information contained in the telemetry signal in a data storage for a future application.

In another example, the headpiece unit 106 and the implanted unit 108 are connected via a percutaneous link. In this example, one or more wires connect the headpiece unit 106 to the implanted unit 108. The headpiece unit 106 transfers the stimulation signal and the power signal to the implanted unit 108 via the one or more wires.

Figure 1B:
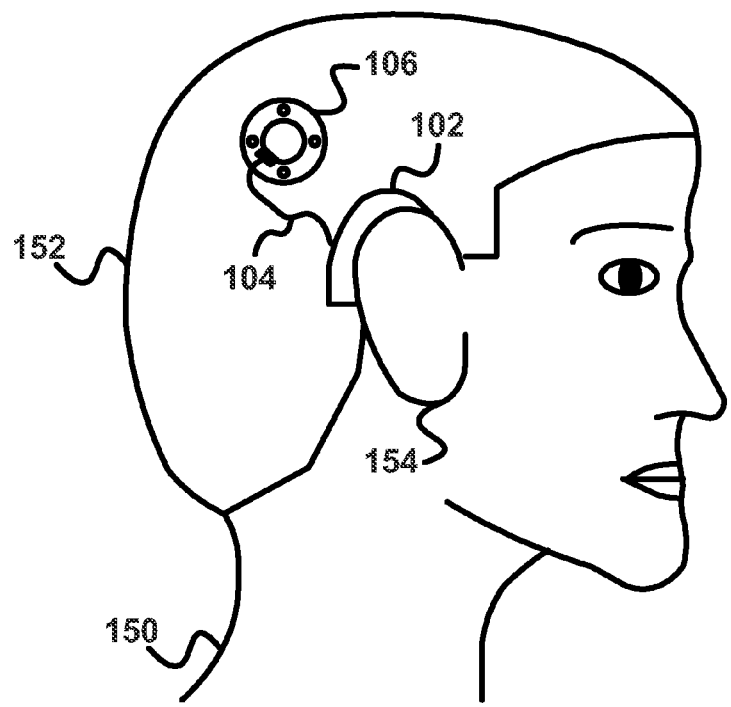
FIG. 1B illustrates a user wearing external components of the hearing prosthesis depicted in FIG. 1A, according to an example.

A user of the hearing prosthesis 100 wears the processing unit 102 and the headpiece unit 106 on the user's head. FIG. 1B illustrates an example of a user 150 wearing some of the components of the first hearing prosthesis 100. The user 150 wears the processing unit 102 at a position on the user's head 152 that allows the processing unit 102 to receive a sound from the environment at a similar incident angle as the user's ear 154. In the illustrated example, the user 150 wears the processing unit 102 behind the user's ear 154. In another example, the user 150 wears the processing unit 102 at a different location on the user's head 152 that is suitable for receiving a sound from the environment.

The headpiece unit 106 is worn on the user's head 152 at a position that is over a location of the user's head 152 at which the implanted unit 108 is implanted. This positioning facilitates the transmission of signals via the first transcutaneous link 130 and transferring the secondary power signal 132. In FIG. 1B, the user 150 wears the headpiece unit 106 on the user's head 152 above and behind the user's ear 154. A portion of the implanted unit 108 is anchored to the user's skull and is directly underneath the illustrated position of the headpiece unit 106. In another example, the headpiece unit 106 and the implanted unit 108 are located at different positions on and in the user's head 152, respectively.

The headpiece unit 106 is magnetically secured to the user's head 152. The headpiece unit 106 and the implanted unit 108 each include one or more magnets. When the headpiece unit 106 is placed over the portion of the user's head 152 at which the implanted unit 108 is implanted, the magnets secure the headpiece unit 106 to the user's head 152. The magnets in the headpiece unit 106 and the implanted unit 108 are shielded to prevent interference with signals over the transcutaneous link 130.

In an alternative example, the headpiece unit 106 and the implanted unit 108 do not include magnets. In this example, the user 150 secures the headpiece unit 106 to the user's head 154 using any method, apparatus, or component suitable for securing the headpiece unit 106 to the user's head 154 over a position at which the implanted unit 108 is implanted.

The user 150 can remove the processing unit 102 and/or the headpiece unit 106 when the user 150 is not utilizing the first hearing prosthesis 100. For instance, the user 150 may remove the processing unit 102 and/or the headpiece unit 106 while the user 150 is sleeping. In one example, the processing unit 102 and/or the headpiece unit 106 are not watertight. The user 150 may remove the processing unit 102 and/or the headpiece unit 106 prior to exposing the user's head 152 to water, such as when the user is swimming or bathing. Additionally, the user 150 may remove the processing unit 102 and/or the headpiece unit 106 in order to charge a rechargeable battery included in the processing unit 102.

Figure 2A:
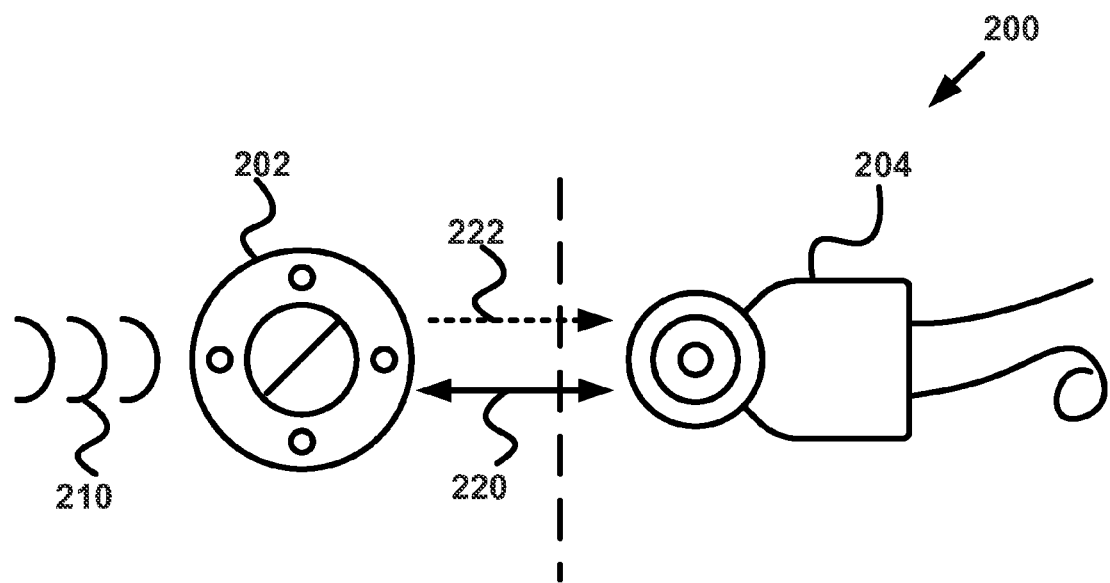
FIG. 2A illustrates components of a second hearing prosthesis, according to an example.

FIG. 2A is illustrates a second hearing prosthesis 200. The second hearing prosthesis 200 includes a processing unit 202 and an implanted unit 204. In the example illustrated in FIG. 2A, the second hearing prosthesis 200 is a partially implantable cochlear implant. In another example, the second hearing prosthesis 200 is a bone conduction device, direct acoustic stimulation device, an auditory brain stem implant, a middle ear implant, or any other hearing prosthesis or combination of hearing prostheses now known or later developed. The processing unit 202 is external to the user's body, and the implanted unit 204 is implanted in the user's body. In an example in which the second hearing prosthesis 200 is a totally implantable hearing prosthesis, such as a totally implantable cochlear implant, the processing unit 202 is also implanted in the body of the user. Furthermore, the components of the processing unit 202 and the implanted unit 204 may be contained in a single enclosure.

The second hearing prosthesis 200 performs the same or substantially similar functions as the first hearing prosthesis 100 depicted in FIG. 1. The primary difference between the second hearing prosthesis 200 and the first hearing prosthesis 100 is that the components of the processing unit 102 and the headpiece unit 106 are contained in a single enclosure, namely the processing unit 202. The implanted unit 204 is the same as or is substantially similar to the implanted unit 108 described in FIG. 1A.

The processing unit 202 receives a sound signal 210. In one example, the processing unit 204 receives the sound signal 210 from a source in the environment. In another example, the processing unit 204 receives the sound signal 210 from an external device, such as a device configured to stream audio. The processing unit 202 processes the sound signal 210 and generates a stimulation signal. The stimulation signal is the same as or is substantially similar to the stimulation signal described with respect to FIG. 1A. The processing unit 202 transmits to the implanted unit 204 via a transcutaneous link 220. The transcutaneous link 220 is the same as or is substantially similar to the transcutaneous link 130 described in FIGS. 1A-1B.

The processing unit 202 also inductively transfers a power signal 222 to the implanted unit 202. The power signal 222 is the same as or is substantially similar to the secondary power signal 132 described in FIGS. 1A-1B. The implanted unit 204 receives the stimulation signal and the power signal 222 and generates a stimulus. The stimulus is the same as or is substantially similar to the stimulus described with respect to FIG. 1A. The implanted unit 204 delivers the stimulus to an auditory organ, such as a cochlea, allowing the user to perceive at least a portion of the sound 210.

In another example, the processing unit 202 and the implanted unit 204 are connected via a percutaneous link. In this example, one or more wires connect the processing unit 202 to the implanted unit 204. The processing unit 202 transfers the stimulation signal and the power signal to the implanted unit 204 via the one or more wires.

Figure 2B:
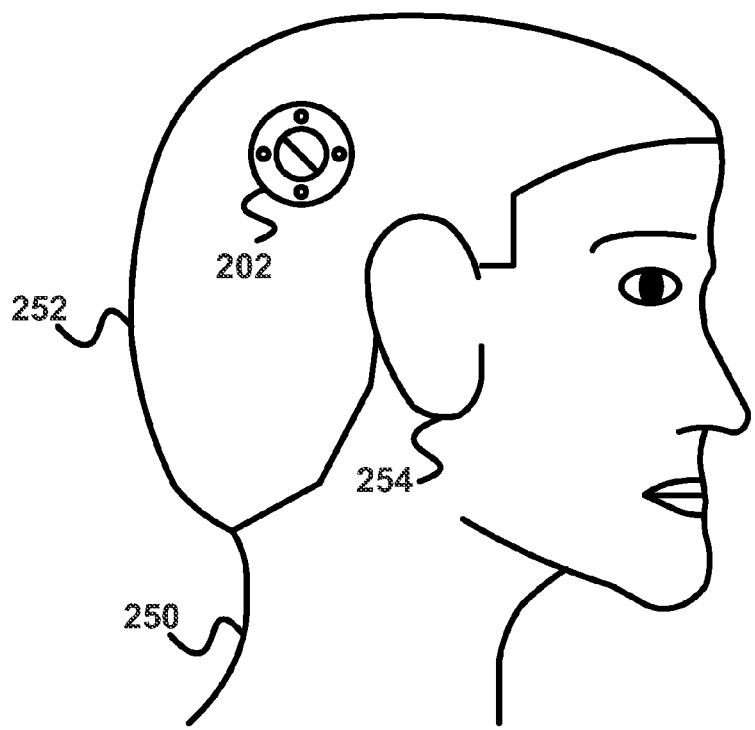
FIG. 2B illustrates a user wearing an external component of the second hearing prosthesis depicted in FIG. 2A, according to an example.

FIG. 2B illustrates an example of a user 250 wearing the processing unit 202 of the second hearing prosthesis 200. In this example, the user 250 wears the processing unit 202 on the user's head 252 above and behind the user's ear 254. In another example, the user 250 wears the processing unit 202 at a different position on the user's head 252 that is suitable for receiving sounds and transferring the stimulation signal and the power signal to the implanted unit 204.

The implanted unit 204 is implanted in and secured to user's head 252 in the same or a substantially similar manner as the headpiece unit 106 described in FIGS. 1A-1B. Additionally, the user 250 wears the processing unit 202 in the same or a substantially similar manner as the headpiece unit 106 depicted in FIGS. 1A-1B. Thus, the user 250 may remove the processing unit 202 when the user 250 is not using the second hearing prosthesis 200.

2. Example Components Used in the Hearing Prosthesis

Figure 3:
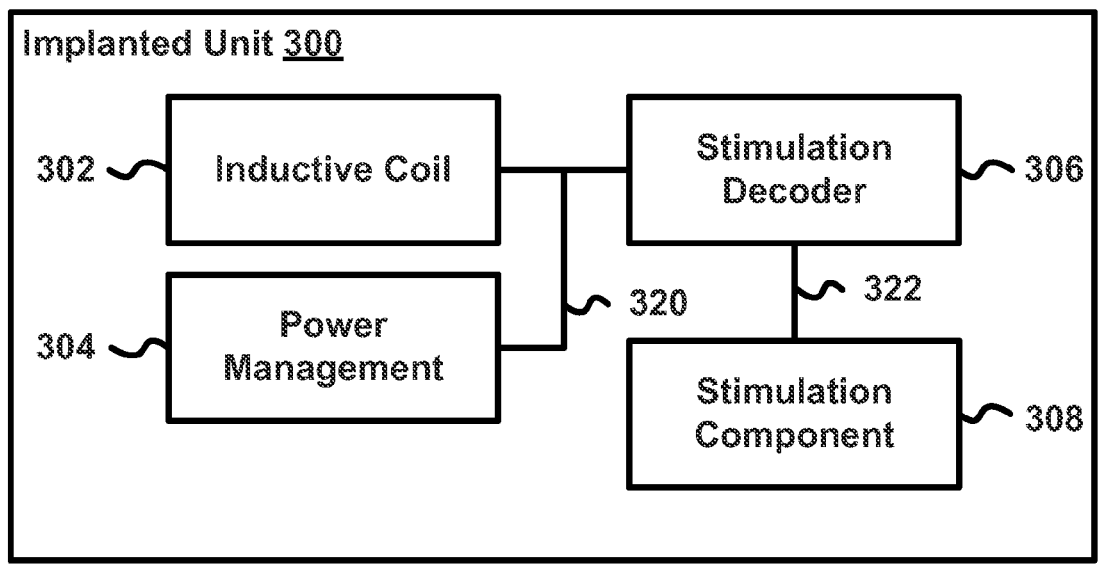
FIG. 3 is a block diagram of an implanted unit depicted in either of FIG. 1A or 2A, according to an example.

FIG. 3 is block diagram of an implanted unit 300. The implanted unit 300 is one example of the implanted units 108 and 204 depicted in FIGS. 1A, 2A, respectively. The implanted unit 300 includes an inductive coil 302, a power management 304, and a stimulation decoder 306, all of which are connected directly or indirectly via circuitry 320. The implanted unit 300 also includes a stimulation component 308 that is connected to the stimulation decoder 306 via circuitry 322.

The inductive coil 302 receives a modulated power signal from an external unit, such as one of the headpiece unit 106 and the processing unit 202 depicted in FIGS. 1A-2B. The modulated power signal includes both a power signal and a stimulation signal. The inductive coil 302 is constructed of any material or combination of materials suitable for inductively receiving power from the external unit. The inductive coil 302 transfers the modulated power signal to the power management 304.

The power management 304 receives the modulated power signal from the inductive coil 302 and distributes power to the components of the implanted unit 300. The power management 304 includes a component suitable for removing the stimulation signal from the power signal. The power management 304 sends the stimulation signal to the stimulation decoder 306.

In one example, the power management 304 does not contain an independent power source. In this example, the components of the implanted unit 300 do not receive power unless a power signal is received by the inductive coil 302. In another example, the power management 304 includes a supplemental power source, such as a rechargeable battery. The power management 304 supplements the power distributed to the components of the implanted unit 300. For instance, if the power signal received at the inductive coil 302 has a low voltage, the power management 304 supplements the voltage of the power signal to allow for continued operation of the implanted unit 300.

The stimulation decoder 306 receives the stimulation signal from the power management 304. The stimulation decoder 306 decodes the stimulation signal and transfers the stimulation signal to the stimulation component 308. The stimulation decoder 306 also receives a telemetry signal from the stimulation component 308. The stimulation decoder 306 is configured to encode the telemetry signal and send the encoded telemetry signal to the external unit via the induction coil 302 according to a time-division multiple-access ("TDMA") scheme, though other schemes for two-communication may also be used. In an example in which the power signal is not modulated, the stimulation decoder 308 may be replaced with components configured to communicate with the external unit, such as a transceiver and an antenna.

The stimulation component 308 receives the stimulation signal from the stimulation decoder 306 and generates a stimulus based on the stimulation signal. In one example, the stimulation component 308 includes a first subcomponent configured to generate the stimulus and a second subcomponent configured to deliver the stimulus to an auditory organ, such as a cochlea, an auditory nerve, a brain, and any other organ or body part capable of assisting a user of the hearing prosthesis in perceiving at least a portion of a sound. The first subcomponent generates the stimulus based on the stimulation signal and sends the stimulus to the second component. The second subcomponent delivers the stimulus to the body part of the user.

For instance, if implanted unit 300 is part of a cochlear implant, the stimulation component 308 includes a signal generator and an electrode array that is implanted in a cochlea of the user. The signal generator generates an electrical signal based on the stimulation signal and sends the electrical signal to the electrode array. The electrical signal causes one or more electrodes located on the electrode array to deliver an electrical stimulus to a portion of the user's cochlea. The stimulus causes the cochlea to stimulate an auditory nerve, thereby allowing the user to perceive a least a portion of a sound.

In another example, the stimulation component 308 stimulates a different body part of the user. For instance, if the hearing prosthesis is an auditory brain stem implant, the stimulation component 308 provides the stimulation signal directly to the user's brain. In this case, the stimulation component 308 includes an electrode array that is implanted in the user's brain. The electrical signal is sent to electrode array, causing one or more electrodes located on the array to deliver an electrical stimulus to a portion of the user's brain. The stimulus causes the user to perceive at least a characteristic of the sound.

The stimulation component 308 also generates the telemetry signal. In one example, the stimulation component 308 includes a third subcomponent configured to monitor a plurality of parameters associated with generating and delivering the stimulus. The plurality of parameters may include an output voltage, an output current, a line impedance, or any other parameter associated with generating and delivering the stimulus. The third subcomponent generates the telemetry signal, which includes telemetry data based on one or more parameters of the plurality of parameters. The stimulation component 308 sends the telemetry signal to the stimulation decoder 306.

Figure 4:
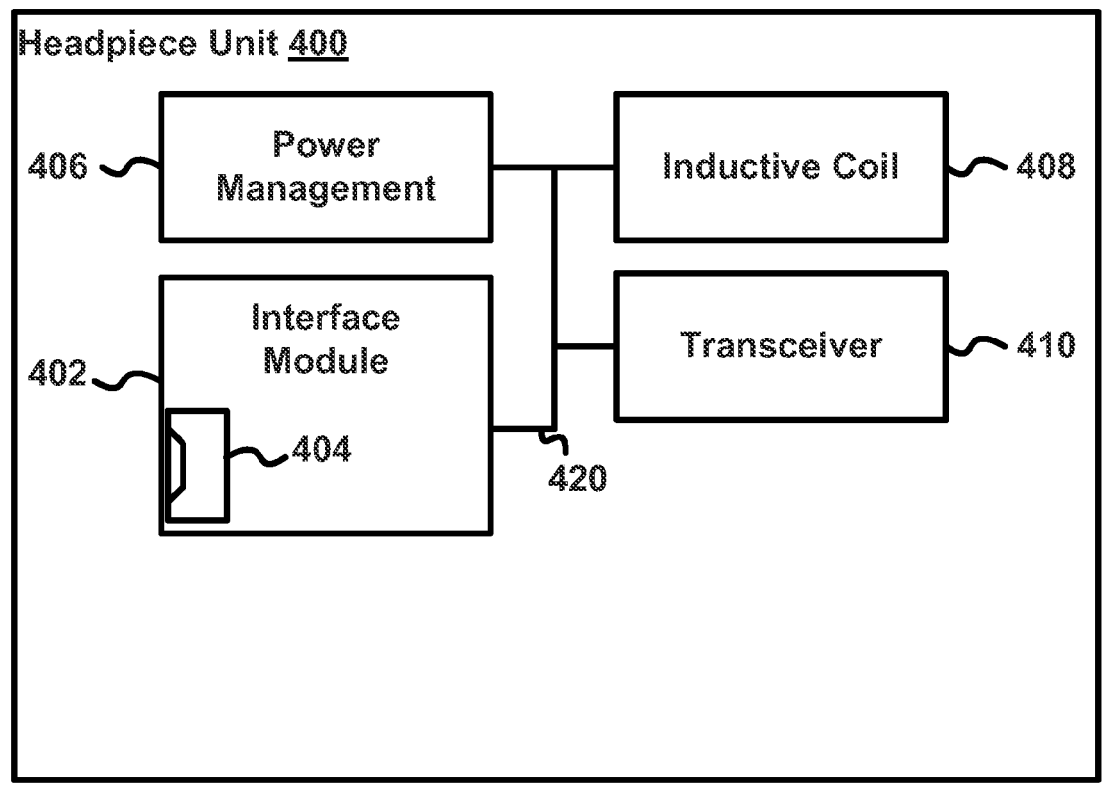
FIG. 4 is a block diagram of a headpiece unit depicted in FIG. 1A, according to an example.

FIG. 4 is a block diagram of a headpiece unit 400. The headpiece unit 400 is one example of the headpiece unit 106 depicted in FIGS. 1A-1B. The headpiece unit 400 includes an interface module 402, a power management 406, an induction coil 408, and a transceiver 410, all of which are connected directly or indirectly via circuitry 420.

The interface module 402 connects the headpiece unit 400 to the external unit via a wired connection. The interface module 402 includes a receptacle 404 configured to interface with a plug of a cable, such as the first plug 112 of the cable 104 described with respect to FIG. 1A. When the cable is connected to the external device, inserting the plug into the receptacle 404 allows the interface signal to receive the input signal from and send the output signal to the external device.

In one example, the receptacle 404 conforms to a standardized physical interface, such as a USB physical interface, an RS-232 physical interface, or any other standardized physical interface suitable for simultaneously transferring data and power. In another example, the circuitry of the interface module 402 conforms to a standardized electrical interface, such as a USB serial interface, an RS-232 serial interface, or any other standardized electrical interface suitable for simultaneously transferring data and power. In yet another example, the circuitry of the interface module 402 conforms to a standardized electrical interface, and the receptacle 404 conforms to a standardized physical interface.

Alternatively, one of the components of the interface module 402 conforms to a proprietary protocol. For example, if the circuitry of the interface module 402 conforms to a standardized electrical interface, the receptacle 404 conforms to a proprietary physical interface. As another example, if the receptacle 404 conforms to a standardized physical interface, the circuitry of the interface module 402 conforms to a standardized electrical interface.

The interface module 402 communicates with a second unit. In one example, the second unit is a processing unit of a hearing prosthesis, such as the processing unit 102 depicted in FIGS. 1A-1B. In another example, the second unit is an electronic device, such as a tablet computer, a digital media player, a mobile phone, and the like.

In one example, the interface module 402 is configured to communicate with the second unit using a standardized data protocol. The standard data protocol is a USB data protocol, a UART data protocol, a USART data protocol, or any other standardized protocol suitable for use in a signal that includes data and power. Depending on the standardized protocol used, the interface module 402 includes an interface suitable for communicating with the second unit using the standardized data protocol. For instance, if the interface module 402 communicates with the second unit using a UART data protocol, the interface module 402 includes a UART interface. In another example, the interface module 402 communicates with the second unit using a proprietary data protocol and includes an interface configured to send and receive signals using the proprietary data protocol.

The interface module 402 receives the first transmission signal from the second unit. The interface module 402 separates the first transmission signal into a stimulation signal and a power signal. The interface module 402 sends the power signal to the power management 406, and the interface module 402 sends the stimulation signal to the transceiver 410. The interface module 402 also receives a telemetry signal from the transceiver 410. The interface module 402 processes the telemetry signal according to either a standardized data protocol or a proprietary data protocol. The interface module 402 generates the second transmission signal based on the telemetry signal and sends the output signal to the second unit.

The power management 406 receives the power signal from the interface module 404 and distributes power to the components of the headpiece unit 400. In one example, the power management 406 does not contain an independent power source. In this example, the components of the headpiece unit 400 do not receive power unless a power signal is included in the input signal. In another example, the power management 406 includes an independent power source, such as a rechargeable or non-rechargeable battery. The power management 406 includes a component configured to regulate the power distributed from, and possibly to, the independent power source. In this arrangement, the power management 406 supplies temporary power to the components of the hearing unit 400 if the input signal does not include the power signal. Alternatively, the power management 406 supplements the power provided by the power signal to account for a fluctuation in the power signal.

The inductive coil 408 receives a portion of the power signal from the power supply 406. The inductive coil 408 also receives a modulated stimulation signal from the transceiver 410. The inductive coil 408 inductively transfers the power signal with the modulated stimulation signal to an implanted unit of the hearing prosthesis, such as the implanted unit 108 depicted in FIG. 1A. The inductive coil 408 is constructed of any material or combination of materials suitable for inductively transferring the power signal to the implant component.

The transceiver 410 receives the stimulation signal from the interface module 402 and sends the modulated stimulation signal to the inductive coil 408. The transceiver 410 is configured to modulate the stimulation signal according to any modulation protocol suitable for use in a hearing prosthesis, such as an on-off keying scheme. The transceiver 410 is also configured to transmit the stimulation signal to a TDMA scheme, though similar scheme may also be used. In one example, the transceiver 410 includes an encoder. The encoder encodes the stimulation signal into an encoded stimulation signal, and the transceiver 410 transmits the encoded stimulation.

The transceiver 410 is also configured to receive a telemetry signal from the implanted unit according to the TDMA scheme. The transceiver 410 receives the telemetry signal via the induction coil 408 and sends the telemetry signal to the interface module 402. In one example, the telemetry signal is encoded. In this example, the transceiver 410 includes a decoder. The transceiver 410 decodes the telemetry signal prior to sending the telemetry signal to the interface module 402.

Figure 5:
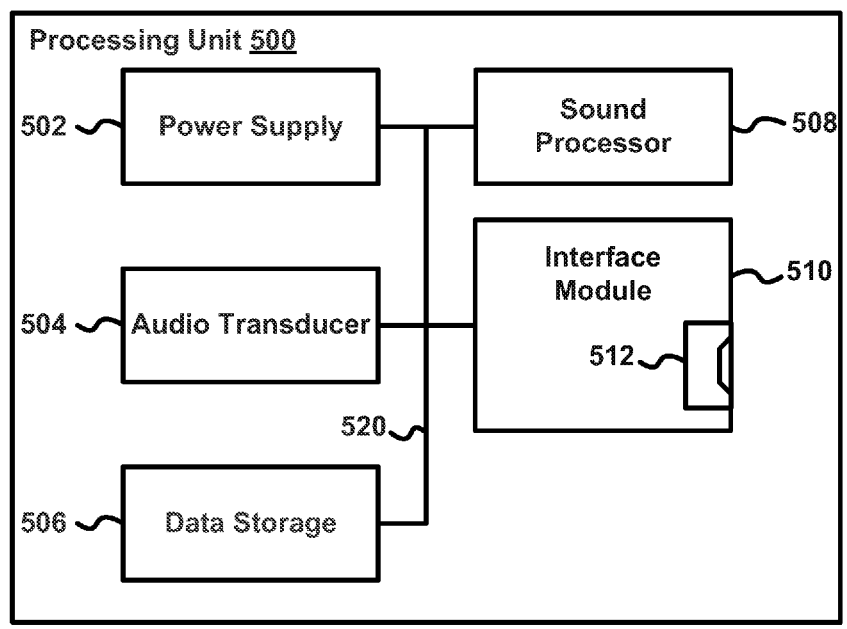
FIG. 5 is a block diagram of a processing unit depicted in FIG. 1A, according to an example.

FIG. 5 is a block diagram of a processing unit 500. The processing unit 500 is one example of the processing unit 102 depicted in FIGS. 1A-1B. The processing unit 500 includes a power supply 502, an audio transducer 504, a data storage 506, a sound processor 508, and an interface module 510, all of which may be connected directly or indirectly via circuitry 520.

The power supply 502 supplies power to various component of the processing unit 500 and can be any suitable power supply. The power supply 502 also provides power to a headpiece unit and an implanted unit of the hearing prosthesis, such as the headpiece unit 106 and the implanted unit 108 described with respect to FIGS. 1A-1B. The power supply 502 sends the primary power signal to the interface module 510 for inclusion in a first transmission signal, which also includes a stimulation signal.

In one example, the power supply 502 includes a rechargeable battery. The power supply 502 charges the rechargeable battery by receiving a power signal from an external source, such as a power adapter, a mobile phone, a portable computing device, an audio player, or any other electronic device suitable for use in recharging the battery. In this example, the power supply 502 receives the power signal from the external source via the interface module 510. Alternatively, the power supply 502 may include a charging component for receiving the power signal from the external source. Examples of a charging component include a power receptacle, an inductive coil, a proprietary interface, and the like.

In another example, the power supply 502 includes a removable battery. In yet another example, the power supply 502 includes a battery or similar power source that is configured to provide power to the components of the processing unit 500 for the operational lifespan of the processing unit 500.

The audio transducer 504 receives a sound from an environment and sends a first sound signal to the sound processor 508. In one example, the processing unit 500 is a component of a cochlear implant, and the audio transducer 504 is an omnidirectional microphone. In another example, the processing unit 500 is a component of a bone-conduction device, an auditory brain stem implant, a direct acoustic stimulation device, or another hearing prosthesis now known or later developed that is suitable for assisting a user of the hearing prosthesis in perceiving sound. In this example, the audio transducer 504 is an omnidirectional microphone, an electromechanical transducer, or any other audio transducer now known or later developed suitable for use in the type of hearing prosthesis employed. Furthermore, in other examples the audio transducer 504 includes one or more additional audio transducers.

The data storage 506 includes any type of non-transitory, tangible, computer readable media now known or later developed configurable to store program code for execution by a component of the processing unit 500 and/or other data associated with the processing unit 500. The data storage 506 stores information indicating a current setting of a parameter of the processing unit 500, such as a volume setting. In one example, the data storage 506 also stores programs executable by the sound processor 508.

The sound processor 508 receives a sound signal, processes the sound signal, and generates the stimulation signal based on the sound signal. In one example, the sound processor 508 is a digital signal processor. In another example, the sound processor 508 is any processor or combination of processors now known or later developed suitable for use in a hearing prosthesis. Additionally, the sound processor 508 may include additional hardware for processing the sound signal, such as an analog-to-digital converter.

The sound processor 508 receives the first sound signal from the audio transducer 508. The sound processor 508 may also receive a second sound signal from the interface module 510. The second sound signal includes information indicative of audio and is received from an external device configured to transfer audio to the processing unit 500, such as a tablet computer, a mobile phone, a digital media player, a laptop computer, and the like.

In one example, the sound processor 508 preferentially processes the second sound signal over the first sound signal. In this example, the sound processor 508 does not process the first sound signal while receiving the second sound signal from the interface controller 512. In one example, the sound processor deactivates the audio transducer 504 while receiving the second sound signal.

In another example, the sound processor 508 preferentially processes the first sound signal over the second sound signal. In this example, the sound processor 508 does not process the second sound signal while receiving the first sound signal from the audio transducer 504. Alternatively, the sound processor 508 processes the first sound signal and determines whether an amplitude of the first sound signal is greater than or equal to a threshold value. If the amplitude of the first sound signal is greater than or equal to the threshold value, the sound processor 508 processes the first sound signal. Otherwise, the sound processor 508 processes the second signal. As an additional example, the sound processor 508 generates the stimulation signal based on the first signal if the amplitude is greater than the threshold value and generates the stimulation signal based on the second signal if the amplitude is less than the threshold value.

For instance, the user of the hearing prosthesis may watch a video on a tablet computer. The user configures the tablet computer to stream an audio signal to the processing unit 500. The sound processor 508 receives the second sound signal from the interface module 510, and the second sound signal includes the audio signal. The audio transducer 504 receives a first sound and includes the first sound in the first sound signal. The sound processor 508 receives and processes the first sound signal. The sound processor 508 determines whether the amplitude is greater than a threshold value. If the first sound is a bird singing outside of a room in which the user is sitting, for instance, the sound processor 508 may determine that the amplitude of the first sound signal is less than the threshold value. In this case, the sound processor 508 processes the second sound signal and generates the stimulation signal based on the second sound signal. If the first sound is a person standing in the same room as the user who is talking to the user, the sound processor 508 may determine that the amplitude of the first sound signal is greater than or equal to the threshold value. In this situation, the sound processor 508 processes the first sound signal.

In yet another example, the sound processor 508 is configured to simultaneously process the first sound signal and the second sound signal. In this example, the sound processor 508 generates the stimulation signal based on both of the first sound signal and the second signal.

The sound processor 508 accesses the data storage 506 to determine a setting of one of a plurality of parameters used for processing the first sound signal and/or the second sound signal. The plurality of parameters includes a sensitivity, a volume, a frequency range, and the like. In one example, the sound processor 508 uses a first set of settings for the plurality of parameters when processing the first sound signal. The sound processor 508 uses a second set of settings for the plurality of parameters when processing the second sound signal. In another example, the sound processor 508 also executes one or more programs stored in the data storage 506 to process the first sound signal and/or the second signal.

The sound processor 508 generates the stimulation signal based on at least one of the first sound signal and the second sound signal. The stimulation signal includes information necessary for stimulating an auditory organ, such as a cochlea, an auditory nerve, a brain, or any other organ or body part capable of allowing the user to perceive at least a portion of a sound. For instance, if the processing unit 500 is a component of a cochlear implant, the stimulating signal includes information necessary for stimulating the user's cochlea so as to allow the user to perceive the sound. In another example, the stimulating signal includes information for stimulating another auditory organ. The sound processor 508 sends the stimulation signal to the interface module 510 for transmission to another component of the hearing prosthesis, such as the headpiece unit 104 depicted in FIGS. 1A-1B.

Additionally, the sound processor 508 receives the telemetry signal from the interface module 510. The sound processor 508 identifies the telemetry data included in the telemetry signal. The sound processor 508 stores the telemetry data in the data storage 206. In one example, the sound processor 508 uses the telemetry data to generate the stimulation signal. For example, the sound processor 508 determines whether a value of a stimulus parameter included in the telemetry is within a tolerance. If the value of the stimulus parameter is not within the tolerance, the sound processor 508 adjusts one or more parameters of the plurality of parameters used to process at least one of the first sound or the second sound. Alternatively, the sound processor 508 stops generating the stimulation signal upon determining that the value of the stimulus parameter is not within the tolerance.

The sound processor 508 may also receive a control signal from an external device via the interface module 510. For instance, a user of the hearing prosthesis interacts with the external device to increase the volume of sounds perceived by the user. The external device sends a control signal that includes information indicative of a change of the volume parameter to the processing unit 500. The sound processor 508 receives the control signal via the interface module 510. The sound processor 508 applies the change to the volume parameter, perhaps by storing a new volume setting in the data storage 506. The sound processor 508 processes sound signals using the new volume setting until the sound processor 508 receives an additional control signal indicating an additional setting of the volume parameter.

Additionally, the sound processor 508 may send an update signal to the external device via the interface module 510. In one example, the sound processor 508 sends the update signal to acknowledge applying a change to a parameter used to process a sound signal. For instance, if a control signal included information indicative of a change to the volume parameter, the update signal includes information indicating that the sound processor 508 applied the change to the volume parameter.

In another example, the sound processor 508 sends the update signal in response to a status signal from the external device. The status signal includes a request for a current setting of one or more parameters from the plurality of parameters used by the sound processor 508 to process the first sound signal and/or the second sound signal. For example, if the status signal includes a request for a current setting of the volume parameter, the sound processor 508 includes information indicative of the current setting of the volume parameter in the update signal. As another example, if the status signal includes a request for the first sound signal, the sound processor 508 includes information indicative of the first sound signal in the update signal.

The interface module 510 provides a means for the processing unit 500 to send the first transmission signal to and receive a second transmission signal from the headpiece unit, which includes the telemetry signal.

The interface module 510 includes a wired connection to a cable, such as the cable 104 depicted in FIGS. 1A-1B. In one example, the cable is not permanently connected to the processing unit 500. The interface module 510 includes a receptacle 512 configured to interface with a plug of the cable. In one example, the receptacle 512 conforms to a standardized physical interface, such as a USB physical interface, an RS-232 physical interface, or any other standardized physical interface suitable for simultaneously transmitting data and power. In another example, the circuitry of the interface module 510 conforms to a standardized electrical interface, such as a USB serial interface, an RS-232 serial interface, or any other standardized electrical interface suitable for simultaneously transmitting data and power. In yet another example, the circuitry of the interface module 510 and the receptacle 512 conform to standardized interfaces.

Alternatively, one of the components of interface module 510 conforms to a proprietary interface. For example, if the circuitry of the interface module 510 conforms to a standardized electrical interface, the receptacle 512 conforms to proprietary physical interface. As another example, if the receptacle 512 conforms to a standardized physical interface, the circuitry of the interface module 510 conforms to a standardized electrical interface.

In another example, the cable is permanently connected to the processing unit 500. The interface module 510 includes circuitry suitable for connecting the cable to the interface module 510. Additionally, the interface module 510 may not include the receptacle 512. The circuitry may conform to a standardized electrical interface, such as a USB serial interface, an RS-232 serial interface, or any other standardized electrical interface suitable for simultaneously transmitting data and power. Alternatively, the circuitry may conform to an electrical specification of a proprietary serial interface.

The interface module 510 may include multiple receptacles. In one example, the interface module 510 may include the receptacle 512 and a second receptacle. The receptacle 512 connects the processing unit 500 with the headpiece unit, while the second receptacle connects the processing unit 500 to an external device, such as tablet computer, a digital media player, a mobile phone, a laptop, and the like. In yet another example, the interface module 510 includes a wireless interface module. The wireless interface module conforms to a standardized protocol for wireless communication, such as a Bluetooth protocol, a Wi-Fi protocol, a WiMAX protocol, or any other standardized wireless protocol suitable for use in the processing unit 500.

The interface module 510 is configured to send and receive signals, such as the first transmission signal and the second transmission signal, according to a data protocol. In one example, the data protocol is a standardized data protocol, such as a USB data protocol, a UART data protocol, a USART data protocol, or any other standardized data protocol suitable for transmitting data and power. Depending on the standardized protocol used, the interface module 510 includes an interface suitable for sending and receiving signals using the standardized data protocol. For instance, if the interface module 512 uses a USART data protocol, the interface module 510 includes a USART interface. In another example, the interface module 402 sends and receives signals using a proprietary data protocol.

In an example where the interface module 510 includes multiple receptacles, the interface module 510 receives multiple signals from the multiple receptacles. In this example, the interface module 512 is configured to route one or more signals to components of the hearing prosthesis 500.

For instance, an incoming signal from the external device includes an incoming data signal and an incoming power signal. The interface module 510 separates the incoming signal into the incoming data signal and the incoming power signal. The interface module 510 includes at least a first portion of the incoming power signal in the first transmission signal. The interface module controller 510 may also send a second portion of the incoming power signal to the power supply 502. The power supply 502 uses the second portion of the incoming power signal to provide power to the components of the processing unit 500 and/or to charge a rechargeable battery of the power supply 502.

In one example, the incoming data signal includes an audio signal, and the interface module 510 sends the audio signal to the sound processor 508 as the second sound signal. In another example, the incoming data signal includes a control signal, and the interface module 510 sends the control signal to the sound processor 508. In yet another example, the incoming data signal includes a status signal, and the interface module 510 sends the status signal to the sound processor 508.

Figure 6:
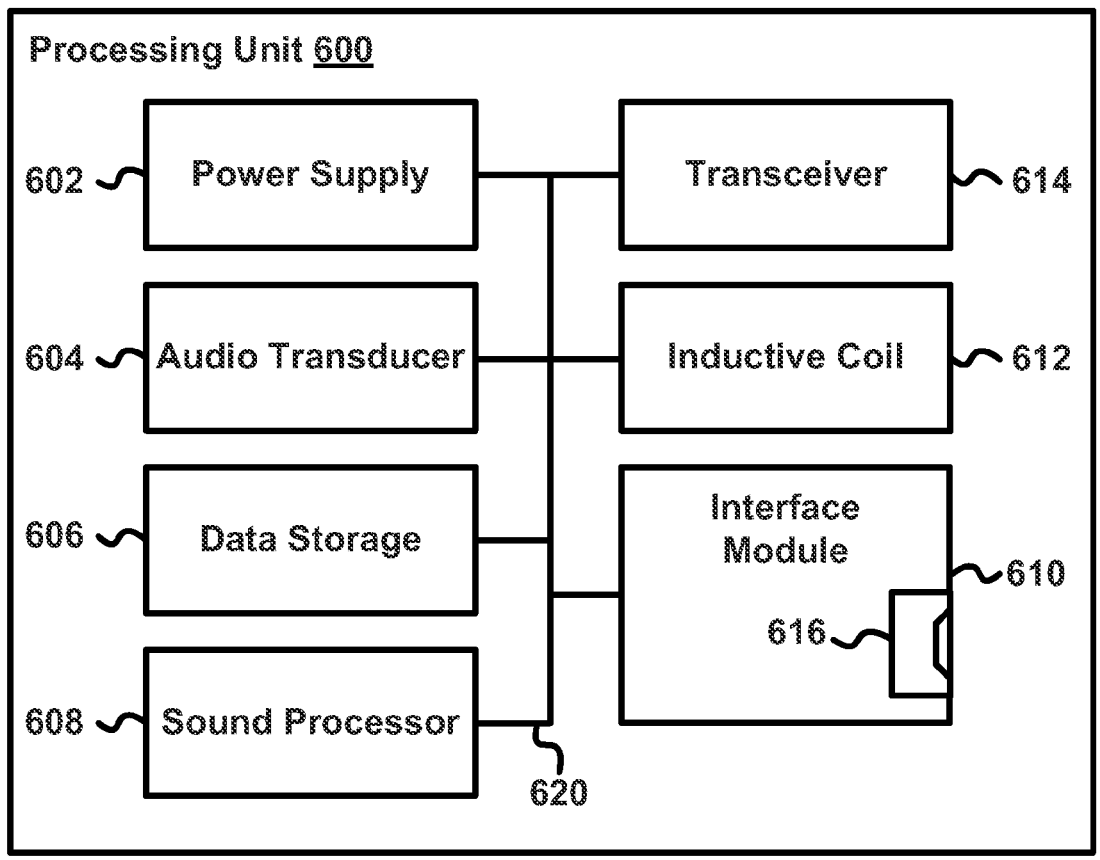
FIG. 6 is a block diagram of a processing unit depicted in FIG. 2A, according to an example.

FIG. 6 is a block diagram of a processing unit 600. The processing unit 600 is one example of the processing unit 202 depicted in FIGS. 2A-2B. The processing unit 600 includes a power supply 602, an audio transducer 604, a data storage 606, a sound processor 608, an interface module 610, an inductive coil 612, and a transceiver 614, all of which may be connected directly or indirectly via circuitry 620.

The processing unit 600 includes the components for processing a sound, communicating with an implanted component of a hearing prosthesis, and transferring a power signal to the implanted component. Thus, the components 602-610 of the processing unit 600 are the same as or are substantially similar to the components 502-510 of the processing unit 500 described with respect to FIG. 5. Additionally, the components 612-614 are the same as or are substantially similar to the components 408-410 of the headpiece unit 400 described with respect to FIG. 4. Furthermore, the receptacle 616 is the same as or is substantially similar to the receptacle 512 described with respect to FIG. 4.

In one example, the processing unit 600 is configured to provide an external device with information indicative of the operation of a component of the processing unit 600. In one example, a cable connects the external device connects to the processing unit 600. The cable is inserted into the receptacle 616 of the interface module 610. The interface module 610 receives a request signal from the external device that includes information indicative of a request for a status of one of the components of the processing unit 600. The interface module 610 routes the request signal the sound processor 608, and the sound processor 608 processes the request signal. The sound processor 608 sends a response signal to the interface module 610 that includes information indicative of the status of the one or more components of the processing unit 600. The interface module 610 sends the response signal to the external device via the cable.

For example, consider a situation in which the external device is configured to perform a diagnostic test on the audio transducer 604. The external device sends the request signal, which includes a request for the first sound signal, to the processing unit 600 via a cable connected to the receptacle 616. The interface module 610 receives the request signal via the receptacle 616 and sends the response signal to the sound processor 608. The sound processor 608, in turn, processes the request signal and sends the response signal to the interface module 610. In this example, the response signal includes the first sound signal. The interface module 610 sends the response signal to the external device via the receptacle 616 and the cable. Upon the external device receiving the response signal, a user of the external device can determine whether the audio transducer 604 is operating properly.

3. Example Applications of a Hearing Prosthesis Utilizing a Standardized Interface A user of a hearing prosthesis may have a plurality of electronic devices capable of providing an audio output. The plurality of electronic devices may include a mobile phone, a tablet computer, an audio player, a portable media player, a laptop computer, a desktop computer, and the like. Additionally, the user of the hearing prosthesis may have an electronic device configured to adjust a parameter used by the hearing prosthesis to process a sound. Including an interface connection that complies with a standardized interface allows the user to utilize one of the plurality of electronic devices without having to acquire a proprietary cable to connect the hearing prosthesis to the electronic device.

For instance, many electronic devices are configured to connect to a computing device. Some electronic devices include a receptacle that conforms to a standard interface, such as a USB. A user of such an electronic device can connect the electronic device to a computer using a standard USB cable.

Other electronic devices connect to a computer via a cable that includes one proprietary plug and one standardized plug. The proprietary plug interfaces with a proprietary receptacle on the electronic device. The standardized plug, which often conforms to a USB interface, interfaces with a standardized receptacle on the computer. Replacement cables or specialty cables are often readily available for use with the electronic devices.

Including a standardized interface connection on a hearing prosthesis allows the user of the hearing prosthesis to connect a variety of electronic devices to the hearing prosthesis with existing cables. The user can also power one or more components of the hearing prosthesis from a connected electronic device that conforms to a standardized interface suitable for transferring data and power. If the hearing prosthesis includes a rechargeable battery, the user may also charge the battery from the electronic device while using the hearing prosthesis.

Figure 7B:
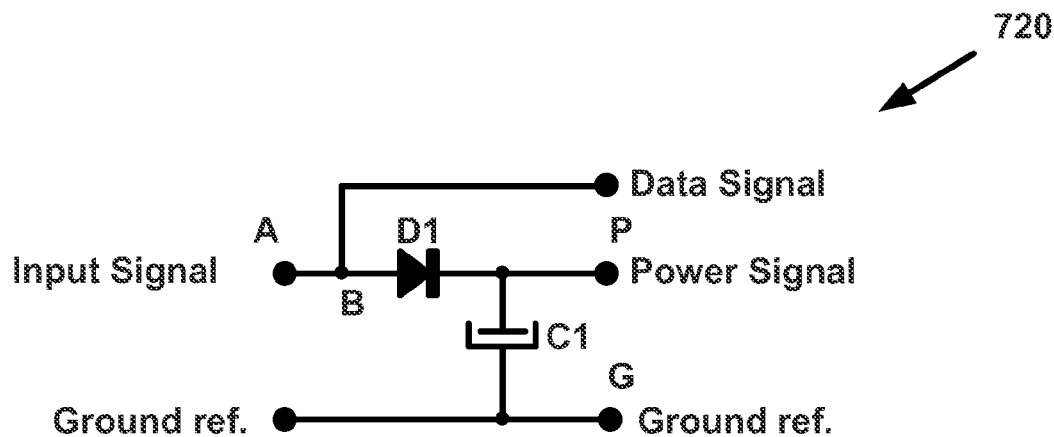
FIG. 7B is an electrical diagram of a component configured to separate a power signal and a data signal, according to an example.
Figure 7A:
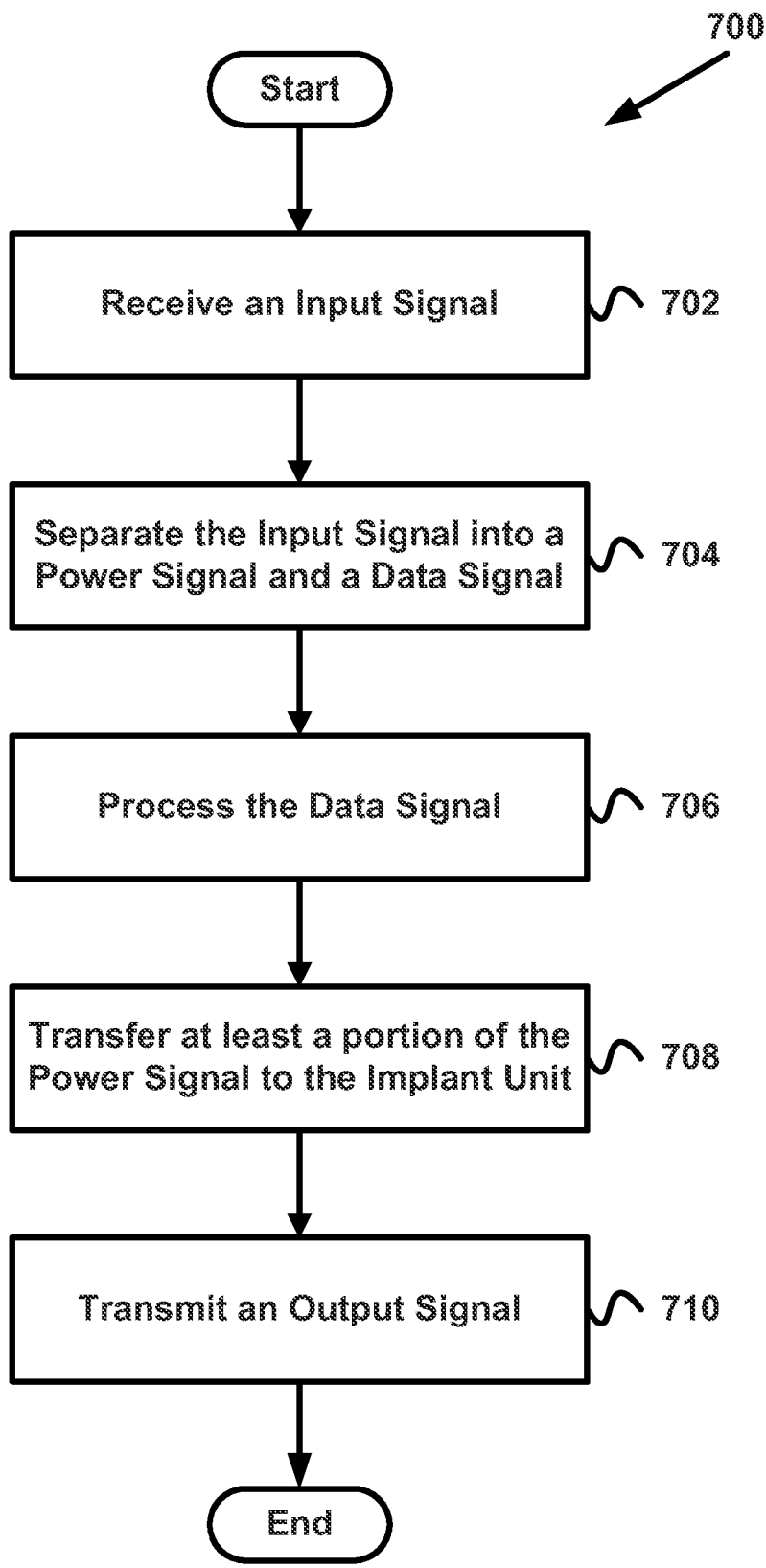
FIG. 7A is a flow diagram of a method for receiving a data signal and a power signal at a wired interface module of a hearing prosthesis that conforms to a standardized interface, according to an example.

FIG. 7A is a flow diagram of a method 700. A component of a hearing prosthesis may utilize the method 700 to receive a data signal and a power signal from an external device via an interface that conforms to a standardized protocol, such as a standardized physical interface, a standardized serial interface, and/or a standardized data protocol. While the first hearing prosthesis 100 and the second hearing prosthesis 200 are used to describe the method 700, it is understood that other devices may be used. For illustrative purposes the headpiece unit 106 includes the components of the headpiece unit 400, and the processing unit 202 includes the components of the processing unit 600.

The method 700 includes one or more operations, functions, or actions as illustrated in blocks 702-710. Although the blocks are illustrated in sequential order, these blocks may be performed in parallel and/or in a different order than those described herein. Also, the various blocks may be combined into fewer blocks, divided into additional blocks, and/or removed based upon the desired implementation.

In addition, for the method 700 and other processes and methods disclosed herein, the flow diagram shows functionality and operation of one possible implementation of one example. In this regard, each block may represent a module, a segment, or a portion of program code, which includes one or more instructions executable by a process for implementing specific logical functions or steps in the process. The program code may be stored on any type of computer readable medium, such as a storage device including a disk or hard drive, for example. The computer readable medium may include non-transitory computer readable media, such as a computer readable media that stores data for a short period of time, such as register memory, processor cache, or Random Access Memory ("RAM"). The computer readable medium may also include non-transitory computer readable media suitable as secondary or persistent long term storage, such as read-only memory ("ROM"), one time programmable memory (OTP), or the like. The computer readable medium may also include any other volatile or non-volatile storage systems. The computer readable medium may be considered computer readable storage medium, for example, or a tangible storage device.

In addition, for the method 700 and other processes and methods discussed herein, each block of FIG. 7A may represent circuitry that is wired to perform the specific logical functions of the process.

At block 702, the method 700 includes a component of a hearing prosthesis receiving an input signal. In one example, processing unit 102 is connected to the headpiece unit 106 by the cable 104. The first plug of the cable 104 is inserted into the first receptacle located on the headpiece unit 104. The processing unit 102 sends the input signal to the headpiece unit 106 via the cable 104, and the headpiece unit receives the input signal at the interface module 402.

In another example, the processing unit 202 is connected to an electronic device via a second cable. The second cable includes a second plug and a third plug. The second plug interfaces with a second receptacle located on the electronic device. The third plug of the second cable interfaces with a third receptacle located on the processing unit 202. At least one of the second cable, the third plug, and the third receptacle conform to one or more standardized interfaces. The processing unit 202 receives the input signal at the interface module 610.

In yet another example, the second cable connects the headpiece unit 106 to the electronic device. In this example, the third plug of the cable is inserted into the first receptacle located on the headpiece unit 106. The headpiece unit 106 receives the input signal at the interface module 402.

At block 704, the method 700 includes separating the input signal into a power signal and a data signal. In one example, the interface module 402 of the headpiece unit 106 separates the input signal into the stimulation signal and the primary power signal. In another example, the interface module 610 of the processing unit 202 separates the input signal into the data signal and the power signal. The interface modules 402, 610 may separate the input signal using a component similar to the component illustrated in FIG. 7B.

FIG. 7B is an electrical diagram of a component 720 configured to separate the input signal into the data signal and the power signal. The component 720 includes a rectifier formed by a diode D1 and a capacitor C1. The data signal is extracted from the input signal at a point B prior upstream of the diode D1. The rectifier removes the data signal from the input signal, allowing the power signal to be extracted at terminal P with respect to the respect to the reference ground G.

Returning to FIG. 7A, the method 700 includes processing the data signal, at block 706. In one example, the interface module 610 of the processing unit 202 identifies the type of data included in the data signal. If the data signal is an audio signal, the interface module 610 sends the audio signal to the sound processor 608 as the second sound signal. If the data signal is a control signal or a status signal, the interface module 610 sends the control signal or the data signal to the sound processor 608. The sound processor 608 processes the second sound signal, the control signal, and the status signal in the same or a substantially similar matter as the sound processor 508 described with respect to FIG. 5.

At block 708, the method 700 includes sending at least a portion of the power signal to the implanted unit. In one example, the power management 406 of the headpiece unit 106 receives the primary power signal from the interface module 402. The power management 406 transfers the secondary power signal, which includes at least a portion of the primary power signal, to the inductive coil 408. The inductive coil 408 inductively transfers the secondary power signal 132 to the processing unit 102 to the implanted unit 408.

In another example, the power supply 602 of the processing unit 202 receives the incoming power signal from the interface controller 612. The power supply 602 transfers a portion of the power signal to the inductive coil 614. The inductive coil 614 transfers the secondary power signal 222 from the processing unit 202 to the implanted unit 204.

At block 710, the method 700 includes transmitting an output signal. In one example, the output signal is the stimulation signal transmitted by the headpiece unit 106 to the implanted unit 108 via the transcutaneous link 130. In another example, the output signal is the stimulation signal transmitted by the processing unit 202 to the implanted unit 204. In yet another example, the output signal is the update signal transmitted by the processing unit 202 to the external device. In this example, the stimulation signal sent from the processing unit 202 to the implanted unit 204 is based on a sound received from an environment.

Figure 8:
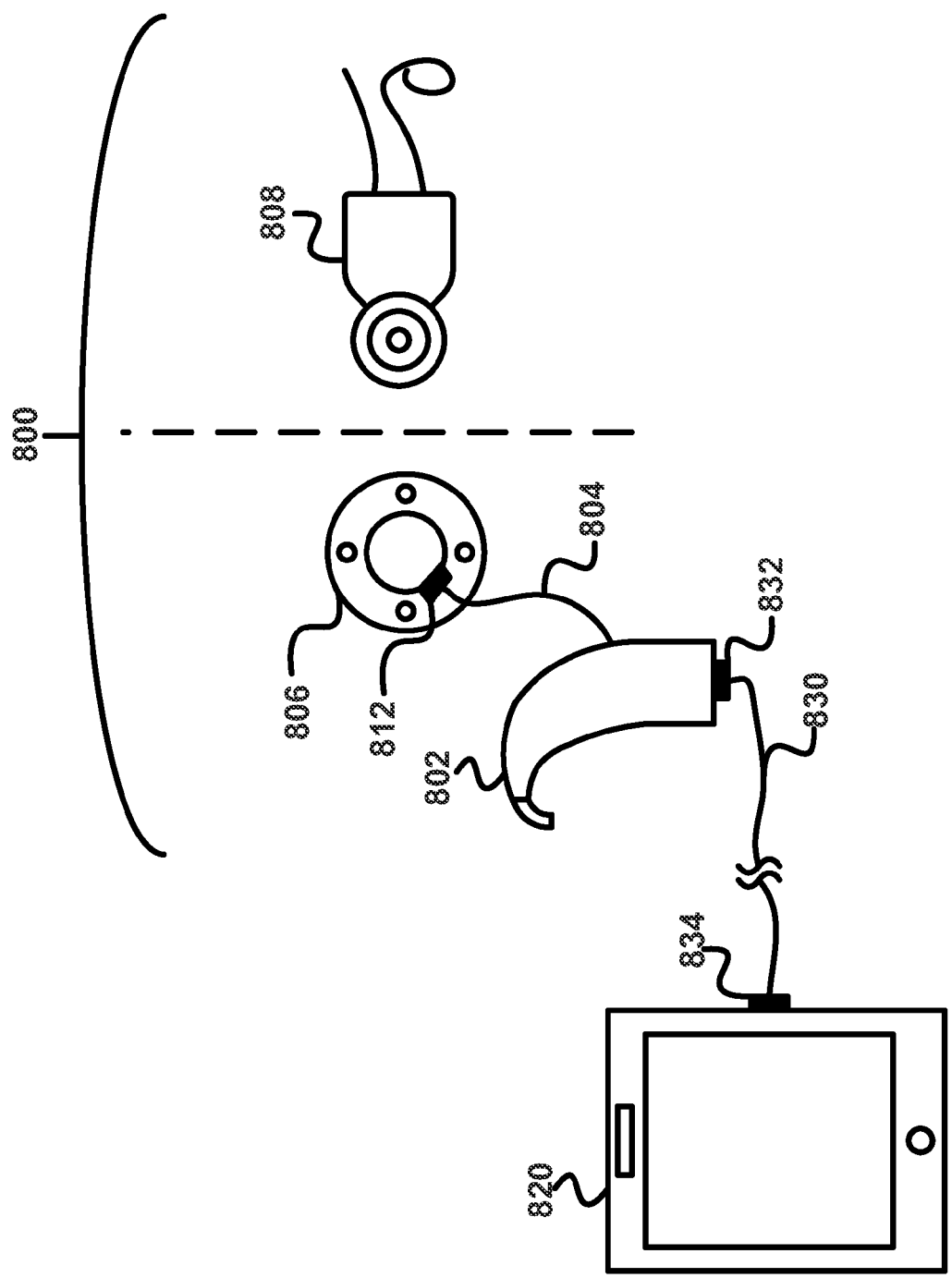
FIG. 8 illustrates a first example of a hearing prosthesis configured to receive a data signal and a power signal at a wired interface module that conforms to a standardized interface.

FIG. 8 illustrates a first example of a hearing prosthesis 800 configured to receive a data signal and a power at an interface that conforms to a standardized interface. The hearing prosthesis 800 includes a processing unit 802, a first cable 804, a headpiece unit 806, and an implanted unit 808. The first cable 804 includes a first plug 812 that is inserted into a first receptacle located on the headpiece unit 806. In this example, the components 802-812 are the same as or are substantially similar to the components 102-112 depicted in FIGS. 1A-1B.

A second cable 830 connects the processing unit 802 to an electronic device 820. In illustrated example, the electronic device 820 is a tablet computer. In another example, the electronic device 820 is a mobile phone, a digital media player, an audio player, or any other portable device cable of transmitting audio to the processing unit 802 via the second cable 830. The second cable 830 includes a second plug 832 and a third plug 834.

In the first example, the second plug 832 conforms to a standardized physical interface. The second plug 832 connects to a second receptacle located on the processing unit 802 that conforms to the same standardized physical interface. For instance, if the second plug 832 is a USB Micro-A plug, the second receptacle on the processing unit 802 is a USB Micro-AB receptacle.

The third plug 834 conforms to either a standardized physical interface or a proprietary physical interface. If the third plug 834 conforms to a standardized physical interface, the third plug 834 connects to a third receptacle located on the electronic device 820 that conforms to the same standardized physical interface. If the third plug 834 conforms to a proprietary physical interface, the third receptacle also conforms to the proprietary physical interface.

In one example, the cable 830 conforms to a standardized electrical interface. In this example, the second plug 832, the second receptacle, the third plug 834, and the third receptacle all conform to the standardized electrical interface. In another example, the cable 830, the second plug 832, the second receptacle, the third plug 834, and the third receptacle conform to an electrical specification of a proprietary serial interface.

In the first example, the user watches a movie on the electronic device 820 while the electronic device is connected to the processing unit 802. The processing unit 820 receives an incoming signal from the electronic device 820. The incoming signal includes an incoming power signal and an audio signal. The incoming power signal provides power to the components of the hearing prosthesis 800. In this example, the incoming power signal also includes a sufficient amount of power to charge a rechargeable battery of the processing unit 802.

The processing unit 802 processes the audio signal and generates the stimulation signal based on the audio signal. The processing unit 802 sends the input signal, which includes the stimulation signal and the primary power signal, to the headpiece unit 806 via the cable 804. The headpiece unit 806 subsequently transmits the stimulation signal to the implant unit 808 and transfers the secondary power signal to the implant unit 808. Thus, the user does not need to remove the processing unit 802 and/or the headpiece unit 806 to charge the battery of the processing unit 802.

Figure 9:
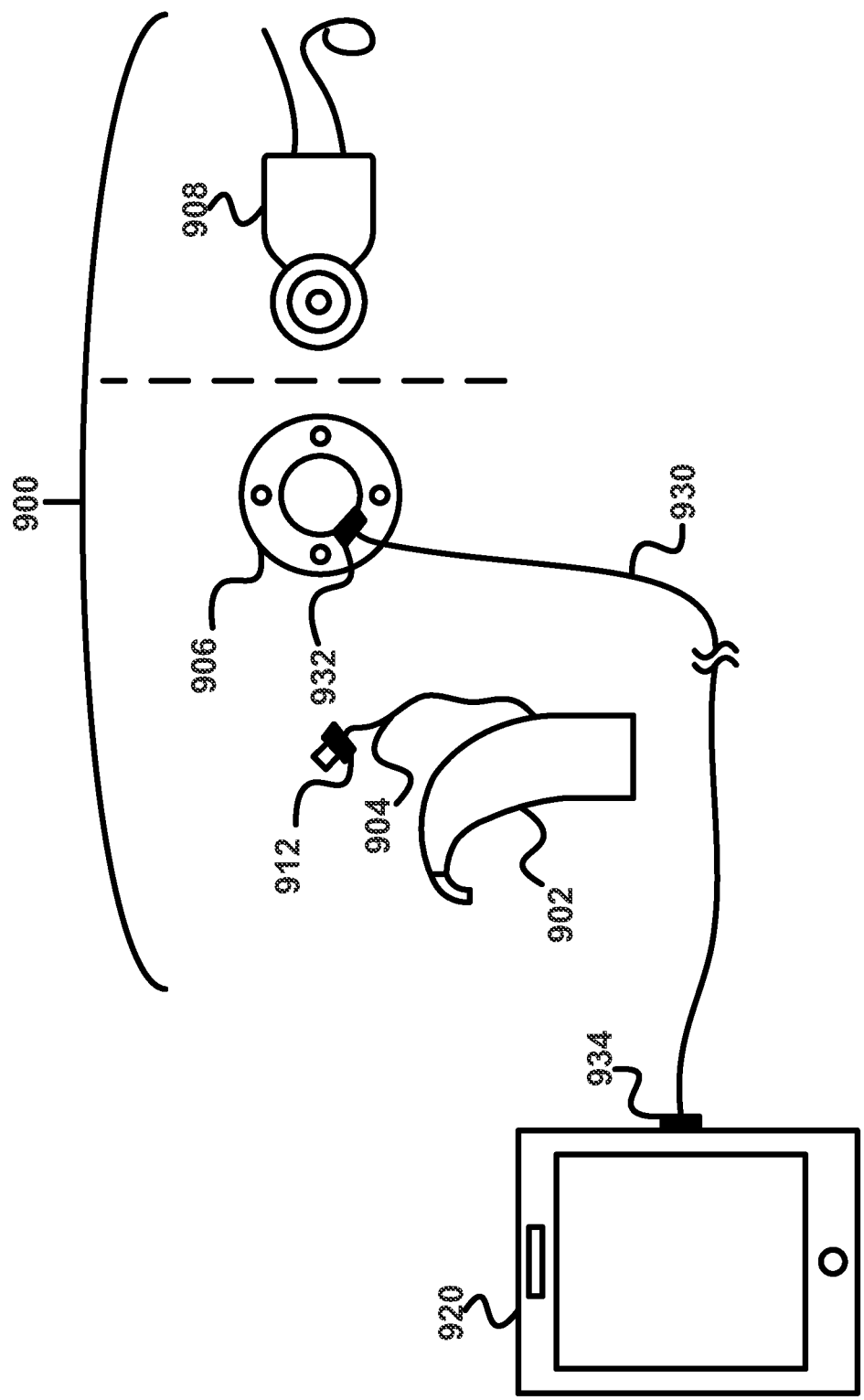
FIG. 9 illustrates a second example of a hearing prosthesis configured to receive a data signal and a power signal at a wired interface module that conforms to a standardized interface.

FIG. 9 illustrates a second example of a hearing prosthesis 900 configured to receive a data signal and a power from an external device at an interface that conforms to a standardized interface. The components 902-934 of the hearing prosthesis 900 are the same as or are substantially similar to the components 802-834 described with respect to the hearing prosthesis 800. In the FIG. 9, the first plug 912 is not connected to the headpiece unit 906. Instead, the second plug 932 of the second cable 930 interfaces with a first receptacle of the headpiece unit 906.

The second example shows how a user of the hearing prosthesis 900 can remove the processing unit 902 while continuing to utilize the headpiece component 906 and the implanted component 908. For instance, the user may wish to charge a rechargeable battery of the processing unit 902 while continuing to watch a movie or listening to music on the electronic device 920.

In this example, the electronic device 920 is configured to generate the stimulation signal. The user connects the electronic device 920 to the headpiece unit 906 via the second cable 930. The electronic device 920 generates an input signal that includes the stimulation signal and the primary power signal signal directly to the headpiece unit 906. The user can then remove the processing unit 902 and charge the battery using a dedicated power source, such as a power adapter. Additionally, charging the battery of the processing unit 902 from a dedicated power source reduces the amount of power consumed by the hearing prosthesis 900, thus prolonging the battery life of the electronic device 920.

Figure 10:
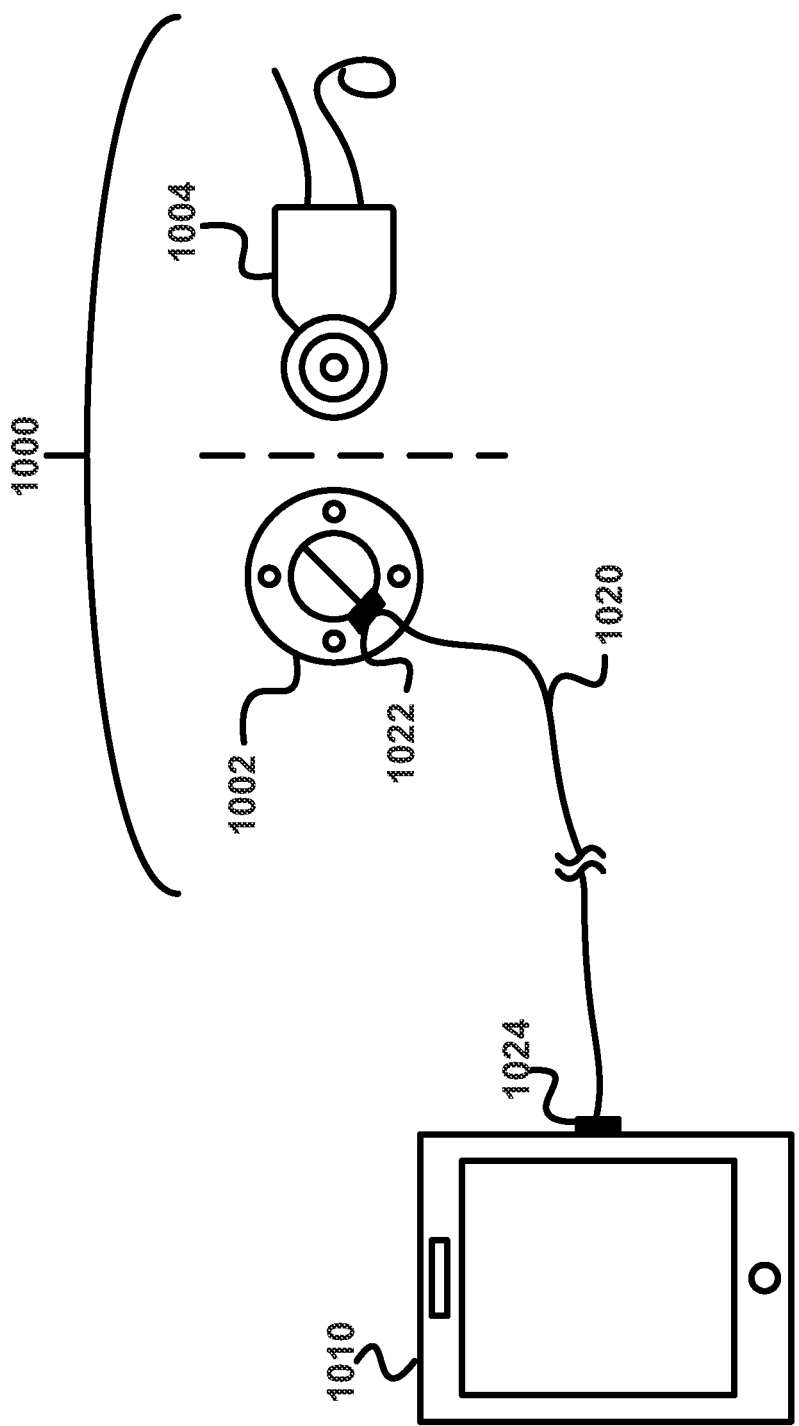
FIG. 10 illustrates a third example of a hearing prosthesis configured to receive a data signal and a power signal at a wired interface module that conforms to a standardized interface.

FIG. 10 illustrates a third example of a hearing prosthesis 1000 configured to receive a data signal and a power signal at an interface that conforms to a standardized interface. The hearing prosthesis 1000 includes a processing unit 1002 and an implanted unit 1004. The processing unit 1002 and the implanted unit 1004 are the same as or are substantially similar to the processing unit 202 and the implanted unit 204 described with respect to FIG. 2A.

A cable 1020 connects the processing unit 1002 to an electronic device 1024. The cable 1020 includes a first plug 1022 and a second plug 1024. The first plug 1022 interfaces with a first receptacle located on the processing unit 1002. The first plug 1022 and the first receptacle conform to a standardized interface. For instance, if the first plug 1022 is a USB Micro A plug, the first receptacle is a USB Micro AB receptacle.

The second plug 1024 conforms to either a standardized physical interface or a proprietary physical interface. If the second plug 1024 conforms to a standardized physical interface, then a second receptacle located on the electronic device 1010 conforms to the same standardized physical interface. If the second plug 1024 conforms to a proprietary physical interface, the second receptacle conforms to the same proprietary physical interface.

In one example, the cable 1020 conforms to a standardized electrical interface. Thus, the first plug 1022, the first receptacle, the second plug 1024, and the second receptacle all conform to the standardized electrical interface. In another example, the cable 1020, the first plug 1022, the first receptacle, the second plug 1024, and the second receptacle conform to a proprietary serial interface.

In the third example, a user of the hearing prosthesis 1000 connects the processing unit 1002 to the electronic device 1010 via the second cable 1020. The electronic device 1010 transfers an input signal to the processing unit 1002 that includes a data signal and an incoming power signal. In one example, the data signal includes an audio signal, such as when the user is watching a video or listening to music on the electronic device 1010. In another example, the data signal includes a control signal, such as when the user is using the electronic device 1010 to fit or calibrate the hearing prosthesis 1000.

The processing unit 1002 receives the data signal and the power signal from the electronic device 1010. The processing unit 1002 inductively transfers at least a first portion of the incoming power signal to the implanted unit 1004. In one example, the processing unit 1002 utilizes a second portion of the incoming power signal to charge a rechargeable battery included in the processing unit 1002. In one example, the user of the hearing prosthesis 1000 watches a movie or listens to music on the electronic device 1010 while electronic device is connected to the processing unit 1002. In this example, the data signal includes an audio signal. The processing unit 1002 generates a stimulation signal based on the audio signal. The processing unit 1002 transmits the stimulation signal to the implanted unit 1004 in addition to transferring the at least the first portion of the incoming power signal to the implanted unit 1004.

In another example, the user utilizes the electronic device 1010 to fit the hearing prosthesis 1000. The processing unit 1002 receives the telemetry data from the implanted unit 1004 and transfers the telemetry data to the electronic device 1010. Based on the telemetry data, the user may cause the electronic device 1010 to send a control signal to the processing unit 1002 that changes one or more parameters from a plurality of parameter used by the processing unit 1002 to process a sound.

Figure 11:
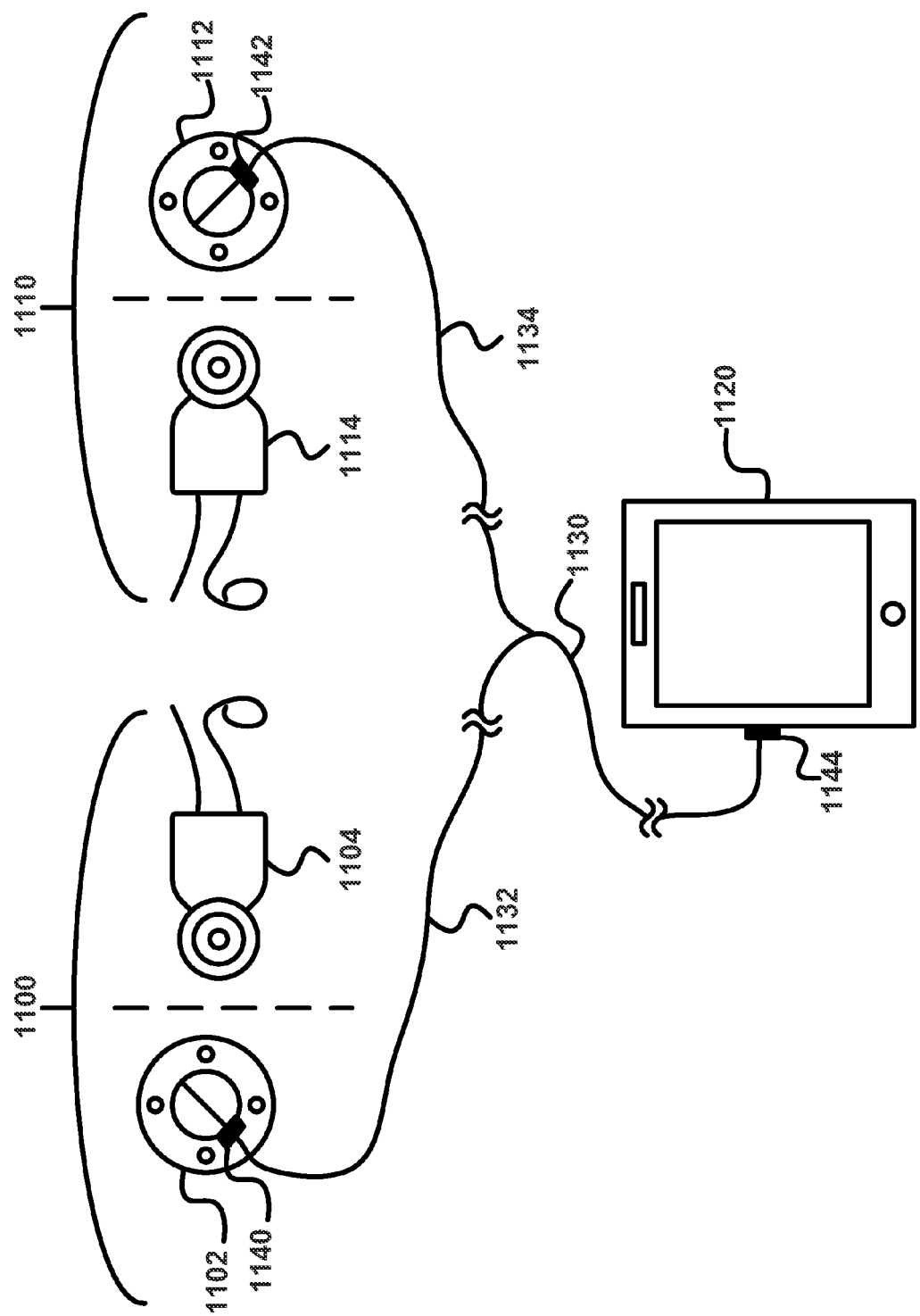
FIG. 11 illustrates a fourth example of hearing prostheses configured to receive a data signal and a power signal at wired interface module that conform to a standardized interface.

FIG. 11 illustrates a fourth example of hearing prostheses 1100, 1110 configured to receive a data signal and a power signal at interfaces that conform to a standardized interface. FIG. 11 includes a first hearing prosthesis 1100 and a second hearing prosthesis 1110 that are part of a bilateral hearing prosthesis system. The bilateral hearing prosthesis system assists a user who suffers from hearing loss in both ears in perceiving a least a portion of a sound. The first hearing prosthesis 1100 includes a first processing unit 1102 and a first implanted unit 1104. The second hearing prosthesis 1110 includes a second processing unit 1112 and a second implanted unit 1114. The processing units 1102, 1112 and the implanted units 1104, 1114 are the same as or are substantially similar to the processing unit 202 and the implanted unit 204 described with respect to FIG. 2A, respectively.

In FIG. 11, the first hearing prosthesis 1100 and the second hearing prosthesis 1110 are connected to an electronic device 1120 via a cable 1130. The cable 1130 includes a first branch 1132 that connects to the first processing unit 1102 and a second branch 1134 that connects to the second processing unit 1112. The cable 1130 conforms to either a standardized electrical interface or a proprietary electrical interface.

The cable 1130 also includes a first plug 1140, a second plug 1142, and a third plug 1144. The first plug 1140 interfaces with a first receptacle located on the first processing unit 1102. Likewise, the second plug 1142 interfaces with a second receptacle located on the second processing unit 1112. The first plug 1140 and the second plug 1142 conform to a standardized interface. The first receptacle and the second receptacle conform to the same standardized interface. For instance, if the first plug 1140 and the second plug 1142 are USB Micro A plugs, the first receptacle and the second receptacle are USB Micro AB receptacles.

The third plug 1144 interfaces with a third receptacle 1144 located on the electronic device 1120. The third plug 1144 and the third receptacle conform to a proprietary mechanical interface. In another example, at least one of the plugs 1140, 1142, 1144 and associated receptacles conform to a standardized mechanical interface and the remaining plugs and receptacles conform to a proprietary mechanical interface.

In FIG. 11, the electronic device 1120 is illustrated as a tablet computer. In another example, the electronic device 1120 is a mobile phone, a digital media player, or another electronic device capable of playing audio. Connecting both processing units 1102, 1112 to the electronic device 1120 allows the user to charge the batteries of the processing units 1102, 1112 while continuing to listen to audio streamed from the electronic device 1120. The user can watch a movie, for example, on the electronic device 1120 while charging the batteries of both processing units 1102, 1112 from the electronic device 1120.

The electronic device 1120 sends a data signal and power signal to each of the processing units 1102, 1112. In one example, the electronic device 1120 is configured to send the data signals to the processing units 1102, 1112 using a standardized data protocol. For instance, the electronic device 1120 may send a first data signal to the processing units 1102, 1112 via the cable 1130. The first data signal is a packet-based signal. The electronic device includes a first address associated with the first processing unit 1102 in a header of a packet in the first data signal.

When the processing units 1102, 1104 receive the first data signal, the processing units 1102, 1104 identify the first address in the first header. The first processing unit 1102 determines that the first address is associated with the first processing unit 1102 and proceeds to process the first data signal. The second processing unit 1112 determines that the first address is not associated with the second processing unit 1112 and does not process the first data signal. Similarly, if the electronic device 1120 includes a second address associated with the second processing unit 1112 in the header of a second data signal, the second processing unit 1112 processes the second data signal and the first processing unit 1102 does not process the second data signal. In another example, the electronic device 1120 and the processing units 1102, 1112 use a different processing scheme or protocol to code and decode data signals sent to the processing units 1102, 1112 via the cable 1130.

The electronic device 1120 may also be configured to control a portion of the functionality of the hearing prostheses 1100, 1110. The electronic device 1120 sends a control signal to one or both of the processing units 1102, 1112 indicating a change in a parameter. In one example, the control signal includes a data packet. The data packet includes an address that is associated with both of the processing units 1102, 1112. In another example, the electronic device 1120 sends a first control signal addressed to the first processing unit 1102 and a second control signal addressed to the second processing unit 1112.

Figure 12:
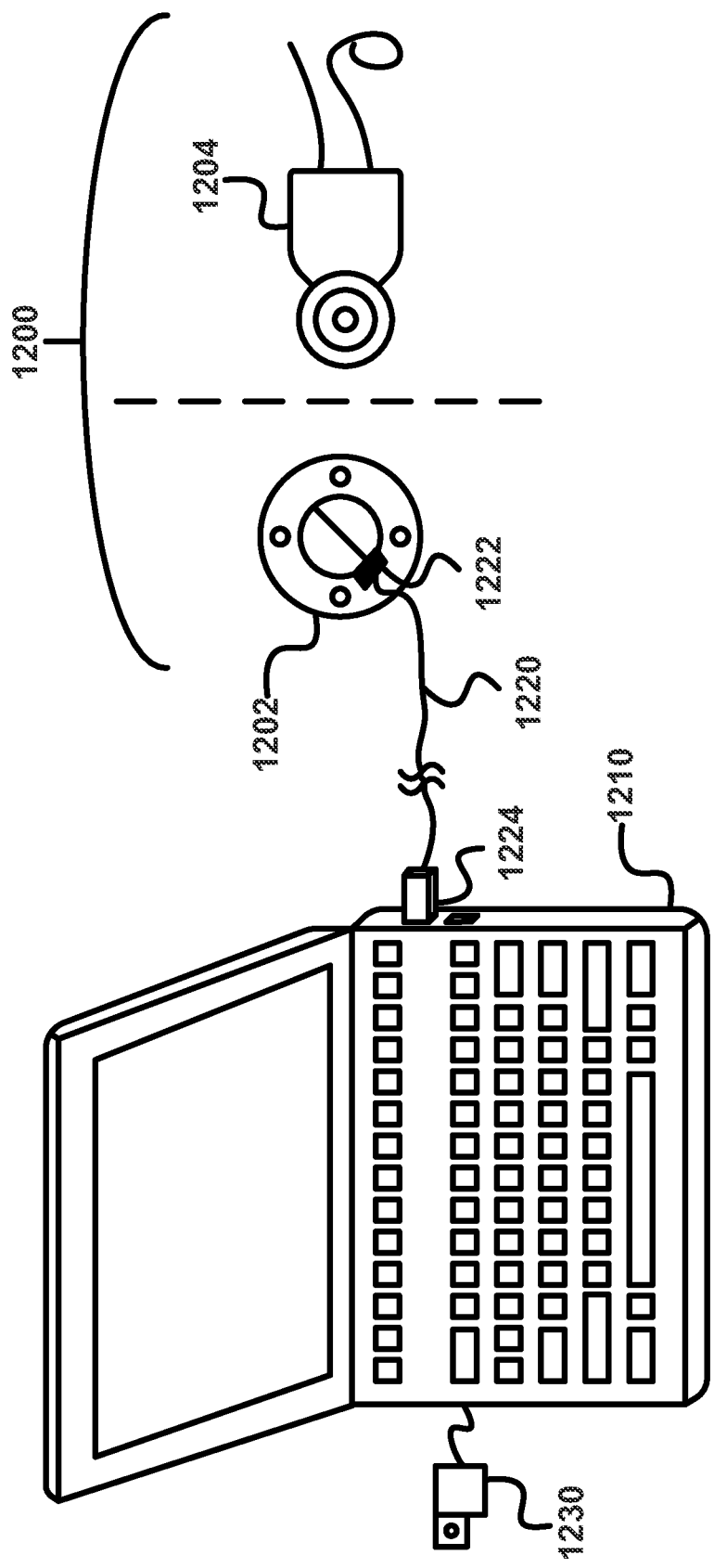
FIG. 12 illustrates a fifth example of a hearing prosthesis configured to receive a data signal and a power signal at a wired interface module that conforms to a standardized interface.

FIG. 12 illustrates a fifth example of a hearing prosthesis system configured to receive a data signal and a power signal at an interface that conforms to a standardized protocol. FIG. 12 includes a hearing prosthesis 1200 connected to a computing device 1210. The hearing prosthesis 1200 includes a processing unit 1202 and an implanted unit 1204. The processing unit 1202 and the implanted unit 1204 are the same as or are substantially similar to the processing unit 202 and the implanted unit 204 described with respect to FIG. 2A.

The computing device 1210, which is illustrated as a laptop computer, is capable of performing the same functions as the any of the electronic devices 820, 920, 1020, 1120 described with respect to FIGS. 8-11. The computing device 1210 is connected to the processing unit 1202 via a cable 1220. The computing device 1210 is also connected to a mains power supply (e.g., 120 V or 240 V power) via the electrical cord and plug 1230. In another example, the computing device 1210 is desktop computer, a netbook computer, a tablet computer, a mobile phone, or any other computing device now known or later discovered that is capable of connecting to a component of a hearing prosthesis and a mains distribution power.

The cable 1220 includes a first plug 1222 that interfaces with a first receptacle located on the processing unit 1202 and a second plug 1224 that interfaces with a second receptacle located on the computing device 1210. In FIG. 12, the first plug 1222, the second plug 1224, the first receptacle, and the second receptacle conform to a standardized physical protocol. In another example, at least one of the plugs 1222, 1224 and associated receptacles conform to a proprietary physical protocol. In an example in which both of the plugs 1222, 1224 and associated receptacles conform to a proprietary physical protocol, the cable 1220 conforms to a standardized electrical protocol. Alternatively, if the plugs 1222, 1224 and associated receptacle conform to a proprietary physical protocol, the computing device 1210 and the hearing prosthesis 1200 communicate using a standardized data protocol.

The computing device 1210 is configured to send and receive data signals to and from the processing unit 1202. The computing device is also configured to send a power signal to the processing unit 1202, allowing the user to charge a battery of the processing unit 1202 while wearing the processing unit 1202. Because the computing device 1210 is connected to the mains distribution power, an isolation component is used to prevent accidental discharge of mains power to the implanted unit 1204.

In FIG. 12, the processing unit 1202 includes the isolation interface. The isolation interface includes one or more components configured to provide the components of the hearing prosthesis 1200 components with reinforced galvanic isolation from the mains distribution power. In one example, the data lines included in an interface module of the processing unit 1202, such as the interface module 610 depicted in FIG. 6, is isolated from the mains power distribution using one or more opto-couplers. The power lines included in the interface module include one or more high frequency isolation transformers. In another example, the isolation interface is included in a different component, such as the first plug 1222 or the second plug 1224.

Other hearing prostheses may be used in any of the preceding applications described with respect to FIGS. 8-12. For instance, in one example the hearing prostheses 1100, 1110 described with respect to FIG. 11 include the components described with respect to FIG. 1A.

Additionally, other applications in which a component of a hearing prosthesis is connected to another device by a cable that conforms to at least one of a standardized mechanical or electrical protocol are possible. For example, a cable configured to connect to one or more interfaces that conform to a standardized protocol connects two hearing prostheses in a bilateral hearing prosthesis system. The cable may connect a first processing unit of a first hearing prosthesis with a second processing unit of a second hearing prosthesis. A user of the bilateral hearing prosthesis system may utilize this arrangement to equalize the charge of the batteries of the hearing prostheses while exchanging data used for processing sound in the bilateral hearing prosthesis system.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method comprising:
   receiving at a wired interface component an input signal, wherein the wired interface component (a) is a component of a first unit of a hearing prosthesis, the first unit being configured to be externally worn by a recipient, and (b) conforms to at least one of a Universal Serial Bus ("USB") protocol or an RS-232 protocol;
   separating the input signal into a data signal and a power signal, wherein the power signal is used to provide power to one or more components of the hearing prosthesis; and
   transferring from the first unit to a second unit of the hearing prosthesis at least a portion of the power signal, wherein the second unit is implanted in the recipient and is configured to stimulate an auditory organ.

2. The method of claim 1, wherein the wired interface component comprises one of a Universal Serial Bus ("USB") physical interface or an RS-232 physical interface.

3. The method of claim 1, wherein the wired interface component comprises one of a USB electrical interface or an RS-232 electrical interface.

4. The method of claim 1, wherein the wired interface component conforms to one of a USB data protocol, a Universal Asynchronous Receiver/Transmitter ("UART") data protocol, or a Universal Synchronous/Asynchronous Receiver/Transmitter ("USART") data protocol.

5. A system comprising:
   an implanted unit configured to (i) receive a stimulation signal, (ii) in response to receiving the stimulation signal, generate a stimulus, and (iii) deliver the stimulus to an auditory organ;
   a headpiece unit comprising a first interface module, the headpiece unit being configured (i) to receive at the first interface module the stimulation signal and a power signal, and (ii) to transmit to the implanted unit the stimulation signal and at least a portion of the power signal; and
   a processing unit comprising a second interface module, the processing unit being configured (i) to generate the stimulation signal based on a sound and (ii) to transfer to the headpiece component via a cable the stimulation signal and the power signal, wherein the cable is connected to the first interface module and the second interface module, and wherein the first interface module and the second interface module conform to one of a USB data protocol, a UART data protocol, or a USART data protocol.

6. The system of claim 5, wherein at least one of the first interface module or the second interface module conforms to one or more physical specifications of a standardized physical interface protocol.

7. The system of claim 5, wherein at least one of the first interface module or the second interface module conforms to one or more electrical specifications of a standardized electrical interface protocol.

8. The system of claim 5, wherein:
   the headpiece unit includes a first inductive coil, wherein the headpiece unit transmits via the first inductive coil the stimulation signal and the portion of the power signal, and
   the implanted unit includes a second inductive coil, wherein the implanted unit receives via the second inductive coil the stimulation signal and the portion of the power signal.

9. The system of claim 8, wherein:
   the implanted unit is further configured to transmit via the second inductive coil a telemetry signal, wherein the telemetry signal includes information indicative of a parameter used by the implanted unit for generating the stimulus, and the headpiece unit is further configured to receive via the first inductive coil the telemetry signal and to transfer the telemetry signal to the processing unit via the cable.

10. A system comprising:
an implanted unit configured to deliver a stimulus to an auditory organ; and
a processing unit configured to:
  receive, at a wired interface module, an input signal from an external device that includes a data component and a power component, wherein the wired interface module conforms to at least one of a USB physical interface protocol, a USB electrical interface protocol, a USB data protocol, an RS-232 physical interface protocol, an RS-232 electrical interface protocol, a UART data protocol, or a USART data protocol;
  separate the input signal into the data component and the power component,
  wherein the power component is used to provide power to at least one component of the system; and
  transfer to the implanted unit at least a portion of the power component,
  wherein the implanted unit is implanted in a body of a recipient, and
  wherein the processing unit is externally worn by the recipient.

11. The system of claim 10, wherein the wired interface module conforms to one or more physical specifications of one of the USB physical interface protocol or the RS-232 physical interface protocol.

12. The system of claim 10, wherein the wired interface module conforms to one or more electrical specifications of one of the USB electrical interface protocol or the RS-232 electrical interface protocol.

13. The system of claim 10, wherein the input signal conforms to one of the USB data protocol, the UART data protocol, or the USART data protocol.

14. The system of claim 10, wherein the processing unit is further configured to:
  generate a stimulation signal that includes information indicative of the stimulus; and
  transmit the stimulation signal to the implanted unit, wherein the implanted unit is configured to receive the stimulation signal.

15. The system of claim 14, wherein, to generate the stimulation signal, the processing unit is configured to:
  identify an audio signal included in the data component of the input signal; and
  process the audio signal, wherein the stimulation signal is based on the audio signal.

16. The system of claim 15, wherein the processing unit comprises an audio transducer, and wherein the processing unit is further configured to preferentially process the audio signal over a sound signal received from an audio transducer.

* * * * *